United States Patent [19]
Takahashi et al.

[11] Patent Number: 6,023,497
[45] Date of Patent: Feb. 8, 2000

[54] APPARATUS FOR DETECTING FOREIGN MATTER WITH HIGH SELECTIVITY AND HIGH SENSITIVITY BY IMAGE PROCESSING

[75] Inventors: Yoshifumi Takahashi, Isehara; Ken Shioiri, Atsugi, both of Japan

[73] Assignee: Anritsu Corporation, Tokyo, Japan

[21] Appl. No.: 09/051,899

[22] PCT Filed: Dec. 25, 1996

[86] PCT No.: PCT/JP96/03778

§ 371 Date: Apr. 17, 1998

§ 102(e) Date: Apr. 17, 1998

[87] PCT Pub. No.: WO98/11456

PCT Pub. Date: Mar. 19, 1998

[30] Foreign Application Priority Data

Sep. 12, 1996 [JP] Japan ................................. 8-265254

[51] Int. Cl.[7] ............................ G01V 5/00; G01N 23/04; G06T 1/00
[52] U.S. Cl. ............................... 378/57; 378/53; 382/110; 382/132
[58] Field of Search .................... 378/57, 58, 53, 378/62, 98.12; 382/110, 120, 132, 141, 143

[56] References Cited

U.S. PATENT DOCUMENTS 5,585,603  12/1996  Vogeley, Jr. ................................. 378/54

FOREIGN PATENT DOCUMENTS

| | | |
|---|---|---|
| 63-79042 | 4/1988 | Japan . |
| 63-236989 | 10/1988 | Japan . |
| 2-266248 | 10/1990 | Japan . |
| 3-291776 | 12/1991 | Japan . |
| 5-223750 | 8/1993 | Japan . |
| 7-85245 | 3/1995 | Japan . |
| 8-145904 | 6/1996 | Japan . |

*Primary Examiner*—David P. Porta
*Assistant Examiner*—Drew A. Dunn
*Attorney, Agent, or Firm*—Frishauf, Holtz, Goodman, Langer & Chick, P.C.

[57] ABSTRACT

This invention provides a contaminant-detecting apparatus having high selectivity and high sensitivity against a contaminant. A product (1) is conveyed to a point where it is irradiated by x-rays from source (3). An x-ray detector (4), having a predetermined detection unit width in a direction perpendicularly intersecting the conveying direction, then detects the x-rays transmitted through the product. A storage unit (5) stores a two-dimensional distribution of x-ray intensity detected by the x-ray detector as a transmission image in units of pixels. An average calculation unit (7) performs a sum-or-product operation of a kernel, which is equal to or larger than 7×7 pixels, (9×9 or 11×11), and equal to or smaller than (a pixel count corresponding to ½ the predetermined x-ray detection unit width)×(pixel count corresponding to ½ the predetermined x-ray detection unit width), and includes a target pixel, in units of pixels of the transmission image stored in the storage unit by using a predetermined coefficient matrix, thereby calculating the weighted average over the kernel. A difference calculation unit (8) calculates the difference between the x-ray intensity of the target pixel of the transmission image stored in the storage unit and the weighted average over the kernel of the target pixel which is calculated by the difference calculation unit. A determination unit (9) compares the difference calculated by the difference calculation unit with predetermined criteria, thereby determining presence/absence of a contaminant in the product to be tested.

11 Claims, 18 Drawing Sheets

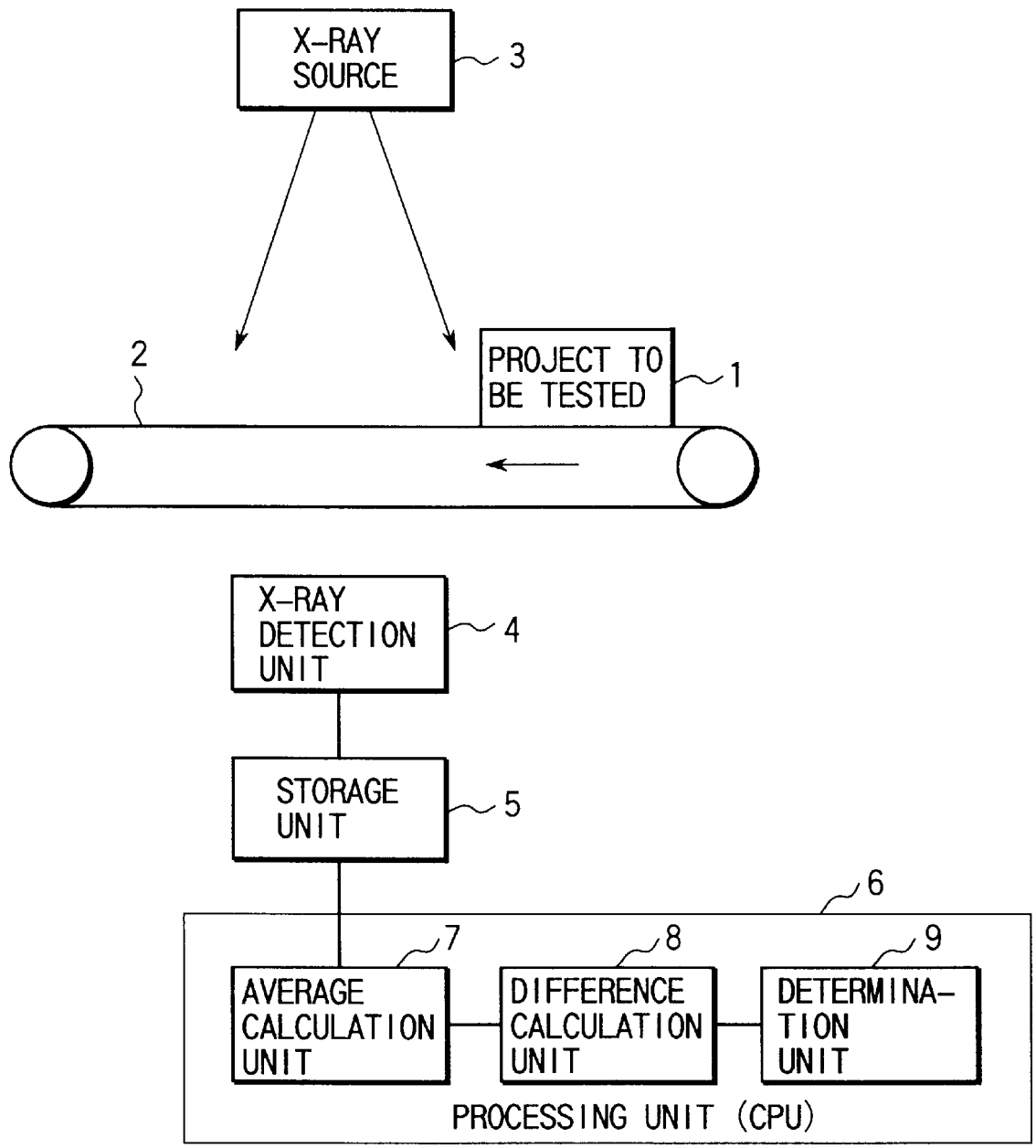
F I G. 1

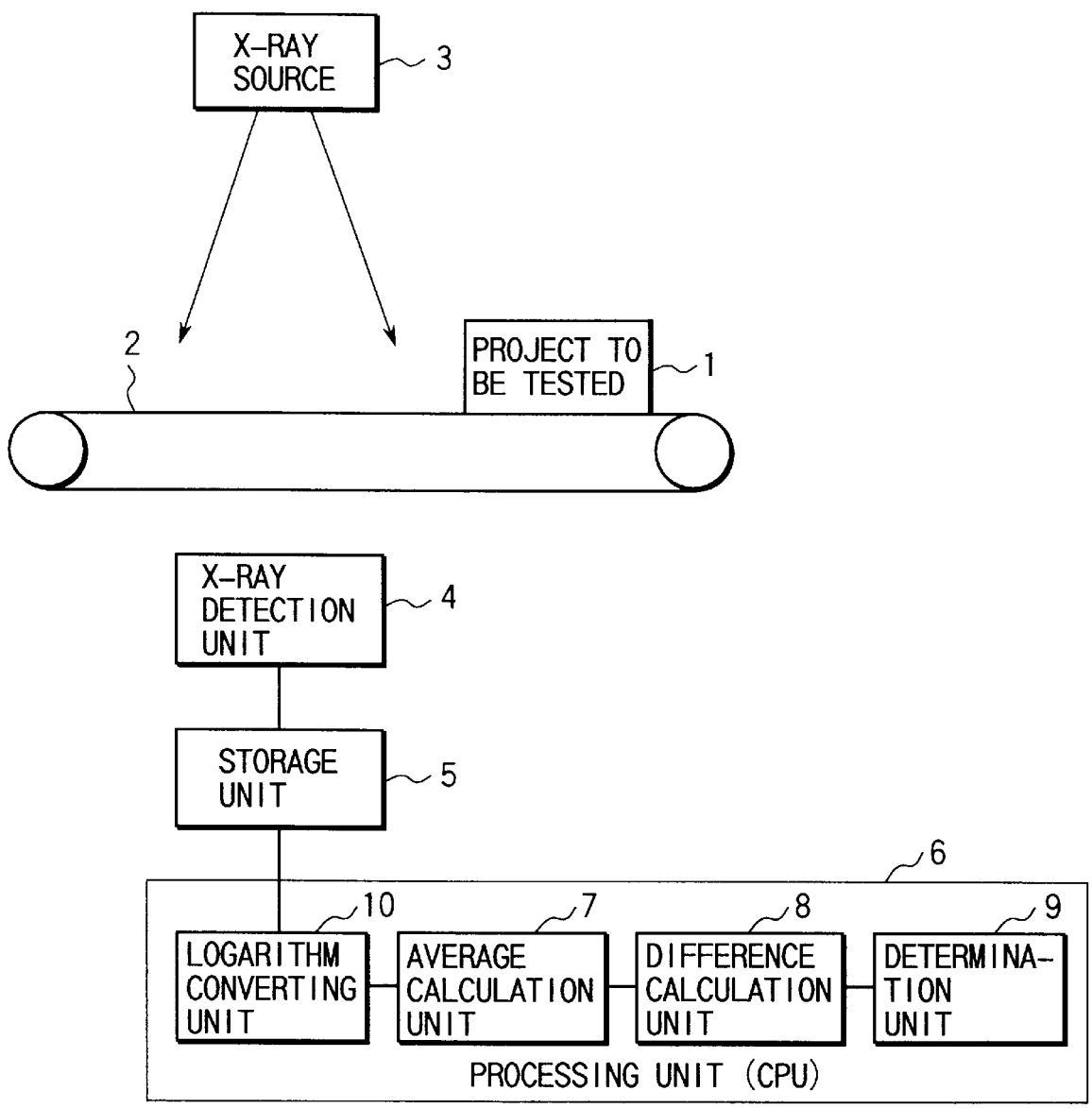
F I G. 2

$$\begin{pmatrix} 1 & 1 & 1 & 1 & 1 & 1 & 1 \\ 1 & 1 & 1 & 1 & 1 & 1 & 1 \\ 1 & 1 & 1 & 1 & 1 & 1 & 1 \\ 1 & 1 & 1 & 1 & 1 & 1 & 1 \\ 1 & 1 & 1 & 1 & 1 & 1 & 1 \\ 1 & 1 & 1 & 1 & 1 & 1 & 1 \\ 1 & 1 & 1 & 1 & 1 & 1 & 1 \end{pmatrix}$$

F I G. 3

$$\begin{pmatrix} 1 & 0 & 1 & 0 & 1 & 0 & 1 \\ 0 & 1 & 0 & 1 & 0 & 1 & 0 \\ 1 & 0 & 1 & 0 & 1 & 0 & 1 \\ 0 & 1 & 0 & 1 & 0 & 1 & 0 \\ 1 & 0 & 1 & 0 & 1 & 0 & 1 \\ 0 & 1 & 0 & 1 & 0 & 1 & 0 \\ 1 & 0 & 1 & 0 & 1 & 0 & 1 \end{pmatrix}$$

F I G. 4

$$\begin{pmatrix} 1 & 1 & 1 & 1 & 1 & 1 & 1 \\ 1 & 0 & 0 & 0 & 0 & 0 & 1 \\ 1 & 0 & 0 & 0 & 0 & 0 & 1 \\ 1 & 0 & 0 & 0 & 0 & 0 & 1 \\ 1 & 0 & 0 & 0 & 0 & 0 & 1 \\ 1 & 0 & 0 & 0 & 0 & 0 & 1 \\ 1 & 1 & 1 & 1 & 1 & 1 & 1 \end{pmatrix}$$

F I G. 5

$$\begin{pmatrix} 0 & 0 & 1 & 1 & 1 & 0 & 0 \\ 0 & 1 & 0 & 0 & 0 & 1 & 0 \\ 1 & 0 & 0 & 0 & 0 & 0 & 1 \\ 1 & 0 & 0 & 0 & 0 & 0 & 1 \\ 1 & 0 & 0 & 0 & 0 & 0 & 1 \\ 0 & 1 & 0 & 0 & 0 & 1 & 0 \\ 0 & 0 & 1 & 1 & 1 & 0 & 0 \end{pmatrix}$$

F I G. 6

F I G. 7

$$\begin{pmatrix} 10 & 5 & 2 & 1 & 2 & 5 & 10 \\ 5 & 0 & -3 & -4 & -3 & 0 & 5 \\ 2 & -3 & -6 & -7 & -6 & -3 & 2 \\ 1 & -4 & -7 & 0 & -7 & -4 & 1 \\ 2 & -3 & -6 & -7 & -6 & -3 & 2 \\ 5 & 0 & -3 & -4 & -3 & 0 & 5 \\ 10 & 5 & 2 & 1 & 2 & 5 & 10 \end{pmatrix}$$

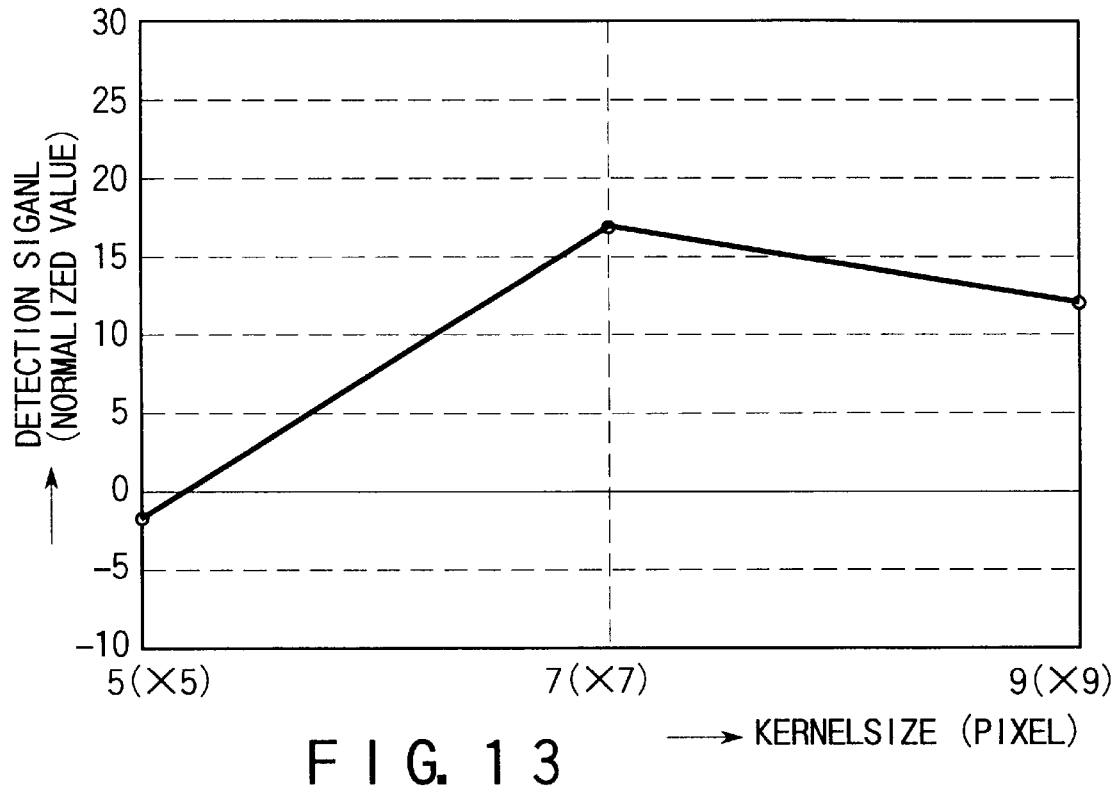
F I G. 1 3
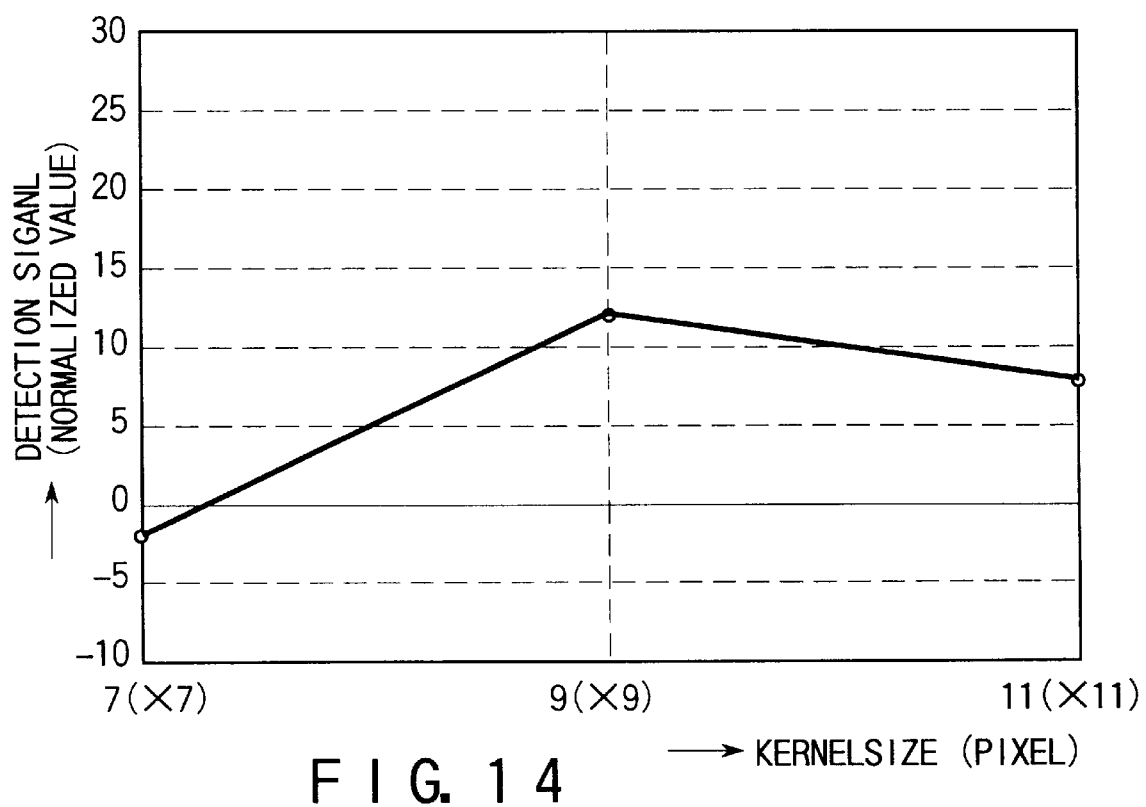
F I G. 1 4

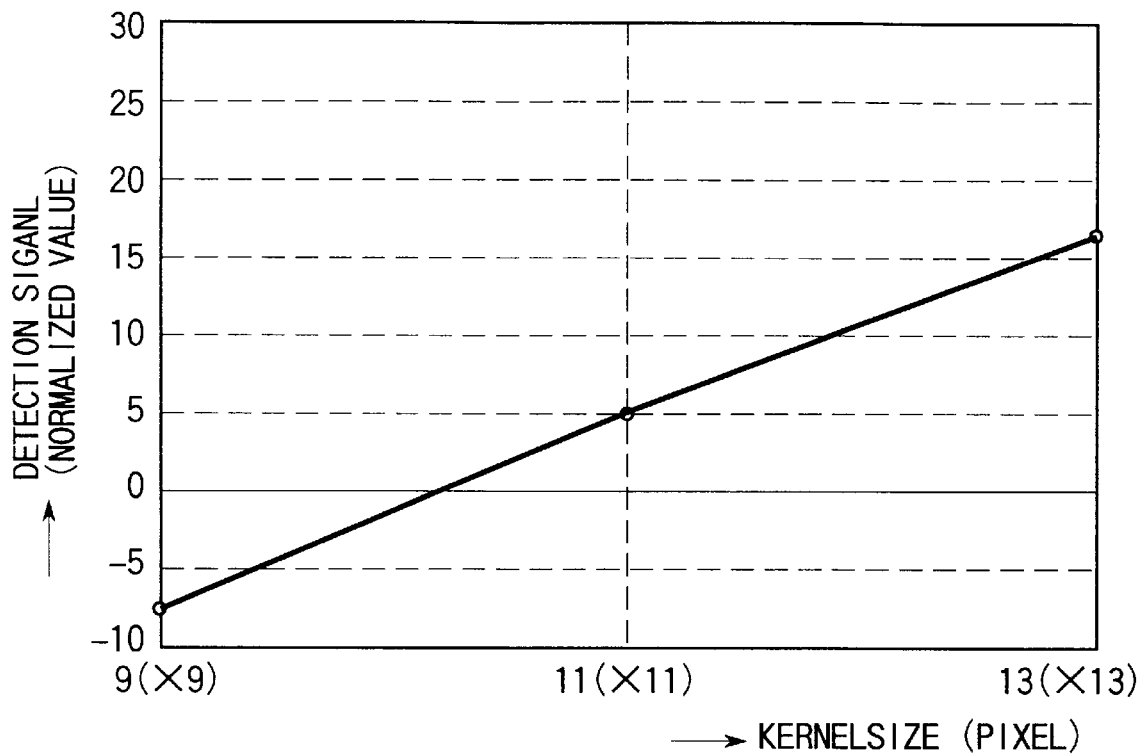
F I G. 15
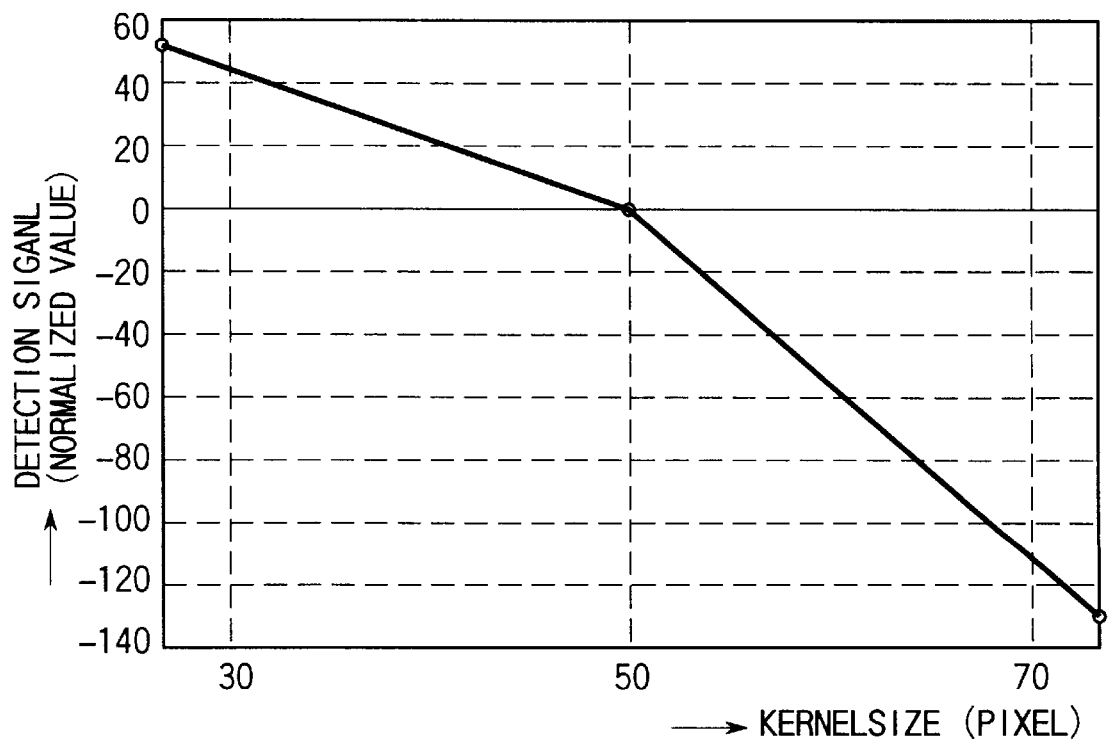
F I G. 16

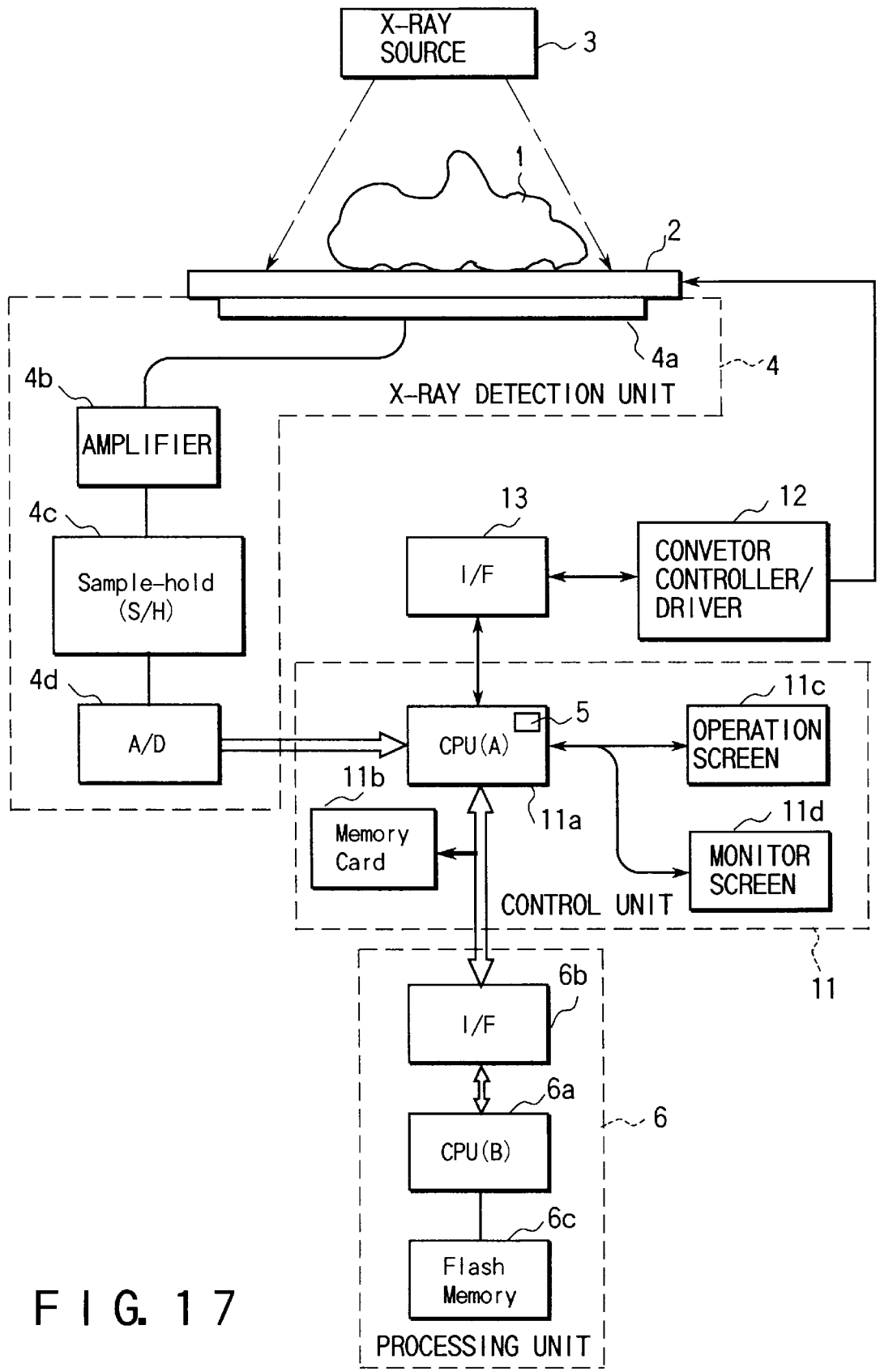
F I G. 17

FIG. 19

$$\begin{pmatrix} 20 & 10 & 5 & 2 & 1 & 2 & 5 & 10 & 20 \\ 10 & 5 & 0 & -3 & -4 & -3 & 0 & 5 & 10 \\ 5 & 0 & -3 & -6 & -7 & -6 & -3 & 0 & 5 \\ 2 & -3 & -6 & -10 & -13 & -10 & -6 & -3 & 2 \\ 1 & -4 & -7 & -13 & 0 & -13 & -7 & -4 & 1 \\ 2 & -3 & -6 & -10 & -13 & -10 & -6 & -3 & 2 \\ 5 & 0 & -3 & -6 & -7 & -6 & -3 & 0 & 5 \\ 10 & 5 & 0 & -3 & -4 & -3 & 0 & 5 & 10 \\ 20 & 10 & 5 & 2 & 1 & 2 & 5 & 10 & 20 \end{pmatrix} 9 \times 9$$

FIG. 20

$$\begin{pmatrix} 1 & 1 & 1 & 1 & 1 & 1 & 1 & 1 & 1 \\ 1 & 1 & 1 & 1 & 1 & 1 & 1 & 1 & 1 \\ 1 & 1 & 1 & 1 & 1 & 1 & 1 & 1 & 1 \\ 1 & 1 & 1 & 1 & 1 & 1 & 1 & 1 & 1 \\ 1 & 1 & 1 & 1 & 1 & 1 & 1 & 1 & 1 \\ 1 & 1 & 1 & 1 & 1 & 1 & 1 & 1 & 1 \\ 1 & 1 & 1 & 1 & 1 & 1 & 1 & 1 & 1 \\ 1 & 1 & 1 & 1 & 1 & 1 & 1 & 1 & 1 \\ 1 & 1 & 1 & 1 & 1 & 1 & 1 & 1 & 1 \end{pmatrix} 9 \times 9$$

FIG. 21

$$\begin{pmatrix} 1 & 0 & 1 & 0 & 1 & 0 & 1 & 0 & 1 \\ 0 & 1 & 0 & 1 & 0 & 1 & 0 & 1 & 0 \\ 1 & 0 & 1 & 0 & 1 & 0 & 1 & 0 & 1 \\ 0 & 1 & 0 & 1 & 0 & 1 & 0 & 1 & 0 \\ 1 & 0 & 1 & 0 & 1 & 0 & 1 & 0 & 1 \\ 0 & 1 & 0 & 1 & 0 & 1 & 0 & 1 & 0 \\ 1 & 0 & 1 & 0 & 1 & 0 & 1 & 0 & 1 \\ 0 & 1 & 0 & 1 & 0 & 1 & 0 & 1 & 0 \\ 1 & 0 & 1 & 0 & 1 & 0 & 1 & 0 & 1 \end{pmatrix} 9 \times 9$$

$$\begin{pmatrix} 1 & 1 & 1 & 1 & 1 & 1 & 1 & 1 & 1 \\ 1 & 0 & 0 & 0 & 0 & 0 & 0 & 0 & 1 \\ 1 & 0 & 0 & 0 & 0 & 0 & 0 & 0 & 1 \\ 1 & 0 & 0 & 0 & 0 & 0 & 0 & 0 & 1 \\ 1 & 0 & 0 & 0 & 0 & 0 & 0 & 0 & 1 \\ 1 & 0 & 0 & 0 & 0 & 0 & 0 & 0 & 1 \\ 1 & 0 & 0 & 0 & 0 & 0 & 0 & 0 & 1 \\ 1 & 0 & 0 & 0 & 0 & 0 & 0 & 0 & 1 \\ 1 & 1 & 1 & 1 & 1 & 1 & 1 & 1 & 1 \end{pmatrix} 9 \times 9$$

F I G. 2 2

$$\begin{pmatrix} 0 & 0 & 0 & 1 & 1 & 1 & 0 & 0 & 0 \\ 0 & 0 & 1 & 0 & 0 & 0 & 1 & 0 & 0 \\ 0 & 1 & 0 & 0 & 0 & 0 & 0 & 1 & 0 \\ 1 & 0 & 0 & 0 & 0 & 0 & 0 & 0 & 1 \\ 1 & 0 & 0 & 0 & 0 & 0 & 0 & 0 & 1 \\ 1 & 0 & 0 & 0 & 0 & 0 & 0 & 0 & 1 \\ 0 & 1 & 0 & 0 & 0 & 0 & 0 & 1 & 0 \\ 0 & 0 & 1 & 0 & 0 & 0 & 1 & 0 & 0 \\ 0 & 0 & 0 & 1 & 1 & 1 & 0 & 0 & 0 \end{pmatrix} 9 \times 9$$

F I G. 2 3

$$\begin{pmatrix} 40 & 20 & 10 & 5 & 2 & 1 & 2 & 5 & 10 & 20 & 40 \\ 20 & 10 & 5 & 3 & -3 & -4 & -3 & 3 & 5 & 10 & 20 \\ 10 & 5 & 3 & 0 & -6 & -8 & -6 & 0 & 3 & 5 & 10 \\ 5 & 3 & 0 & -6 & -13 & -15 & -13 & -6 & 0 & 3 & 5 \\ 2 & -3 & -6 & -13 & -26 & -30 & -26 & -13 & -6 & -3 & 2 \\ 1 & -4 & -8 & -15 & -30 & 0 & -30 & -15 & -8 & -4 & 1 \\ 2 & -3 & -6 & -13 & -26 & -30 & -26 & -13 & -6 & -3 & 2 \\ 5 & 3 & 0 & -6 & -13 & -15 & -13 & -6 & 0 & 3 & 5 \\ 10 & 5 & 3 & 0 & -6 & -8 & -6 & 0 & 3 & 5 & 10 \\ 20 & 10 & 5 & 3 & -3 & -4 & -3 & 3 & 5 & 10 & 20 \\ 40 & 20 & 10 & 5 & 2 & 1 & 2 & 5 & 10 & 20 & 40 \end{pmatrix} 11 \times 11$$

F I G. 24

$$\begin{pmatrix} 1 & 1 & 1 & 1 & 1 & 1 & 1 & 1 & 1 & 1 & 1 \\ 1 & 1 & 1 & 1 & 1 & 1 & 1 & 1 & 1 & 1 & 1 \\ 1 & 1 & 1 & 1 & 1 & 1 & 1 & 1 & 1 & 1 & 1 \\ 1 & 1 & 1 & 1 & 1 & 1 & 1 & 1 & 1 & 1 & 1 \\ 1 & 1 & 1 & 1 & 1 & 1 & 1 & 1 & 1 & 1 & 1 \\ 1 & 1 & 1 & 1 & 1 & 1 & 1 & 1 & 1 & 1 & 1 \\ 1 & 1 & 1 & 1 & 1 & 1 & 1 & 1 & 1 & 1 & 1 \\ 1 & 1 & 1 & 1 & 1 & 1 & 1 & 1 & 1 & 1 & 1 \\ 1 & 1 & 1 & 1 & 1 & 1 & 1 & 1 & 1 & 1 & 1 \\ 1 & 1 & 1 & 1 & 1 & 1 & 1 & 1 & 1 & 1 & 1 \\ 1 & 1 & 1 & 1 & 1 & 1 & 1 & 1 & 1 & 1 & 1 \end{pmatrix} 11 \times 11$$

F I G. 25

$$\begin{pmatrix} 1 & 0 & 1 & 0 & 1 & 0 & 1 & 0 & 1 & 0 & 1 \\ 0 & 1 & 0 & 1 & 0 & 1 & 0 & 1 & 0 & 1 & 0 \\ 1 & 0 & 1 & 0 & 1 & 0 & 1 & 0 & 1 & 0 & 1 \\ 0 & 1 & 0 & 1 & 0 & 1 & 0 & 1 & 0 & 1 & 0 \\ 1 & 0 & 1 & 0 & 1 & 0 & 1 & 0 & 1 & 0 & 1 \\ 0 & 1 & 0 & 1 & 0 & 1 & 0 & 1 & 0 & 1 & 0 \\ 1 & 0 & 1 & 0 & 1 & 0 & 1 & 0 & 1 & 0 & 1 \\ 0 & 1 & 0 & 1 & 0 & 1 & 0 & 1 & 0 & 1 & 0 \\ 1 & 0 & 1 & 0 & 1 & 0 & 1 & 0 & 1 & 0 & 1 \\ 0 & 1 & 0 & 1 & 0 & 1 & 0 & 1 & 0 & 1 & 0 \\ 1 & 0 & 1 & 0 & 1 & 0 & 1 & 0 & 1 & 0 & 1 \end{pmatrix} 11 \times 11$$

F I G. 2 6

$$\begin{pmatrix} 1 & 1 & 1 & 1 & 1 & 1 & 1 & 1 & 1 & 1 & 1 \\ 1 & 0 & 0 & 0 & 0 & 0 & 0 & 0 & 0 & 0 & 1 \\ 1 & 0 & 0 & 0 & 0 & 0 & 0 & 0 & 0 & 0 & 1 \\ 1 & 0 & 0 & 0 & 0 & 0 & 0 & 0 & 0 & 0 & 1 \\ 1 & 0 & 0 & 0 & 0 & 0 & 0 & 0 & 0 & 0 & 1 \\ 1 & 0 & 0 & 0 & 0 & 0 & 0 & 0 & 0 & 0 & 1 \\ 1 & 0 & 0 & 0 & 0 & 0 & 0 & 0 & 0 & 0 & 1 \\ 1 & 0 & 0 & 0 & 0 & 0 & 0 & 0 & 0 & 0 & 1 \\ 1 & 0 & 0 & 0 & 0 & 0 & 0 & 0 & 0 & 0 & 1 \\ 1 & 0 & 0 & 0 & 0 & 0 & 0 & 0 & 0 & 0 & 1 \\ 1 & 1 & 1 & 1 & 1 & 1 & 1 & 1 & 1 & 1 & 1 \end{pmatrix} 11 \times 11$$

F I G. 2 7

$$\left\{ \begin{matrix} 0 & 0 & 0 & 1 & 1 & 1 & 1 & 1 & 0 & 0 & 0 \\ 0 & 0 & 1 & 0 & 0 & 0 & 0 & 0 & 1 & 0 & 0 \\ 0 & 1 & 0 & 0 & 0 & 0 & 0 & 0 & 0 & 1 & 0 \\ 1 & 0 & 0 & 0 & 0 & 0 & 0 & 0 & 0 & 0 & 1 \\ 1 & 0 & 0 & 0 & 0 & 0 & 0 & 0 & 0 & 0 & 1 \\ 1 & 0 & 0 & 0 & 0 & 0 & 0 & 0 & 0 & 0 & 1 \\ 1 & 0 & 0 & 0 & 0 & 0 & 0 & 0 & 0 & 0 & 1 \\ 1 & 0 & 0 & 0 & 0 & 0 & 0 & 0 & 0 & 0 & 1 \\ 0 & 1 & 0 & 0 & 0 & 0 & 0 & 0 & 0 & 1 & 0 \\ 0 & 0 & 1 & 0 & 0 & 0 & 0 & 0 & 1 & 0 & 0 \\ 0 & 0 & 0 & 1 & 1 & 1 & 1 & 1 & 0 & 0 & 0 \end{matrix} \right\} \quad 11 \times 11$$

F I G. 28

APPARATUS FOR DETECTING FOREIGN MATTER WITH HIGH SELECTIVITY AND HIGH SENSITIVITY BY IMAGE PROCESSING

TECHNICAL FIELD

The present invention generally relates to a contaminant-detecting apparatus using X-rays and, more particularly, to a contaminant-detecting apparatus for radiating X-rays toward a product to be tested, e.g., food, conveyed by a conveying means, and processing an obtained X-ray transmission image, thereby detecting a small contaminant, e.g., metal, stone, glass, or the like, mixed in the product to be tested, in real time with high sensitivity.

BACKGROUND ART

As is known, a contaminant-detecting apparatus for determining presence/absence of a contaminant mixed in a product to be tested by using an X-ray transmission image is constituted by a convey means for conveying the product to be tested, an X-ray source means for radiating X-rays toward the product to be tested, an X-ray detecting means for detecting the intensity of X-rays transmitted through the product to be tested, a storage means for storing a signal obtained with the X-ray detecting means as an X-ray transmission image, and a processing means for image-processing the transmission image to determine the presence/absence of a mixed contaminant at high speed.

In a contaminant-determining apparatus of this type, a belt is usually used as the conveying means.

As the X-ray source means, a high-voltage X-ray tube is used which causes electrons, emitted from the high-voltage cathode filament in vacuum, to collide against the metal, e.g., tungsten, of the anode filament, thereby generating X-rays.

As the X-ray detecting means, a linear-array detector arranged perpendicular to the traveling direction of the belt, an X-ray imaging tube, or the like is used.

As the storage means for storing the X-ray transmission image, a semiconductor memory is used.

The processing means is constituted by a feature extracting means, based on image processing techniques, for extracting features from the transmission image, and a determining means for determining the presence/absence of a contaminant by comparing the extracted features with predetermined criteria.

In the conventional contaminant-detecting apparatus having the above arrangement, the contaminant detecting performance is largely influenced by the image processing technique used for extracting the feature from the transmission image.

Various techniques have been proposed as image processing techniques of this type. Most of the image processing techniques proposed so far use a small square pixel kernel of 3×3 pixels.

As an example, a "contaminant-detecting apparatus" disclosed in Jpn. Pat. Appln. KOKAI Publication No. 63-236989 is available.

According to this prior art, a transmission image detected by using radiation is subjected to enhancement, and is thereafter binarized, thereby obtaining a binary image of an object contained in the product to be tested.

Three features, i.e., the area, the peripheral length, and the sum-of-intensity of the object are calculated based on the binary image. These three features are compared with predetermined determination criteria. When the three features satisfy determination conditions, the object is determined to be a contaminant.

In this case, enhancement of the transmission image employs two 3×3 Sobel-filters which respectively perform image enhancement in the vertical and horizontal directions at high speed.

The two images respectively enhanced in the vertical and horizontal directions are finally summed to obtain one enhanced image.

The Sobel-filter is known well as a first-degree-differential-filter for an image, and is often used in image enhancement.

In the field of the conventional contaminant-detecting apparatus using an X-ray transmission image described above, the presence/absence of contaminant must be determined by image-processing a product to be tested, which is being conveyed at a practical belt speed, in real time.

For this reason, as the image processing technique, one using a 3×3 pixel kernel is mainly used since it requires a small number of operations and it can perform high-speed processing, as in the precedent example described above.

More specifically, conventionally, the technique using a kernel equal to or larger than 7×7 pixels, which is employed in the present invention as will be described later, is not considered at all since it requires a large number of operations and can perform processing only at low speed.

Even after a high-speed CPU is introduced and the operations can be performed at a practical speed, a technique using a kernel equal to or larger than 7×7 pixels has not been considered.

In the contaminant-detecting apparatus of this type, when enhancing a transmission image, the density of transmission image of a product to be tested, e.g., food, is sometimes enhanced excessively to obtain a signal indicating as if a contaminant existed.

This signal will be called a false-reject signal. In contrast to this, a signal actually obtained because of the presence of a contaminant will be called a contaminant signal. Conventionally, it is sometimes difficult to discriminate a contaminant signal and false-reject signal from each other.

In other words, the conventional contaminant-detecting apparatus does not perform highly selective image processing, and the contaminant detecting sensitivity is accordingly low.

DISCLOSURE OF INVENTION

It is, therefore, an object of the present invention to provide a novel, useful contaminant-detecting apparatus which is improved to have high selectivity and high sensitivity by employing an image processing technique that can effectively suppress a false-reject signal.

According to the present invention, there is provided a high-selectivity, high-sensitivity contaminant-detecting apparatus for effectively suppressing a false-reject signal, comprising conveying means for conveying a product to be tested in a predetermined convey direction, an X-ray source means for radiating X-rays toward the product to be tested which is being conveyed by the conveying means, X-ray detecting means for detecting the X-rays transmitted through the product to be tested, the X-ray detecting means having an X-ray detection unit with a predetermined detection unit width in a direction perpendicularly intersecting the predetermined convey direction, storage means for storing a two-dimensional distribution of an X-ray intensity detected by the X-ray detecting means as a transmission image in units of pixels, average calculating means for performing a sum-of-product operation for a kernel, which is not smaller than 7×7 pixels and not larger than (a pixel count corresponding to ½ the predetermined X-ray detection unit width)×(a pixel count corresponding to ½ the predetermined X-ray detection unit width), the kernel including a target pixel, in units of pixels of the transmission image stored in the storage means by using a predetermined coefficient matrix, thereby calculating a weighted average over the kernel, difference calculating means for calculating a difference between the X-ray intensity of the target pixel of the transmission image stored in the storage means and the weighted average over the kernel of the target pixel which is calculated by the average calculating means, and determining means for comparing the difference calculated by the difference calculating means with predetermined criteria, thereby determining presence/absence of a contaminant in the product to be tested.

According to the present invention, there is also provided a high-selectivity, high-sensitivity contaminant-detecting apparatus for effectively suppressing a false-reject signal, comprising conveying means for conveying a product to be tested in a predetermined convey direction, an X-ray source means for radiating X-rays toward the product to be tested which is being conveyed by the conveying means, X-ray detecting means for detecting the X-rays transmitted through the product to be tested, the X-ray detecting means having an X-ray detection unit with a predetermined detection unit width in a direction perpendicularly intersecting the predetermined convey direction, storage means for storing a two-dimensional distribution of an X-ray intensity detected by the X-ray detecting means as a transmission image in units of pixels, average calculating means for performing a sum-of-product operation for a kernel, which is not smaller than 9×9 pixels and not larger than (a pixel count corresponding to ½ the predetermined X-ray detection unit width)×(a pixel count corresponding to ½ the predetermined X-ray detection unit width), the kernel including a target pixel, in units of pixels of the transmission image stored in the storage means by using a predetermined coefficient matrix, thereby calculating a weighted average over the kernel, difference calculating means for calculating a difference between the X-ray intensity of the target pixel of the transmission image stored in the storage means and the weighted average over the kernel of the target pixel which is calculated by the average calculating means, and determining means for comparing the difference calculated by the difference calculating means with predetermined criteria, thereby determining presence/absence of a contaminant in the product to be tested.

According to the present invention, there is also provided a high-selectivity, high-sensitivity contaminant-detecting apparatus for effectively suppressing a false-reject signal, comprising conveying means for conveying a product to be tested in a predetermined convey direction, an X-ray source means for radiating X-rays toward the product to be tested which is being conveyed by the conveying means, X-ray detecting means for detecting the X-rays transmitted through the product to be tested, the X-ray detecting means having an X-ray detection unit with a predetermined detection unit width in a direction perpendicularly intersecting the predetermined convey direction, storage means for storing a two-dimensional distribution of an X-ray intensity detected by the X-ray detecting means as a transmission image in units of pixels, average calculating means for performing a sum-of-product operation for a kernel, which is not smaller than 11×11 pixels and not larger than (a pixel count corresponding to ½ the predetermined X-ray detection unit width)×(a pixel count corresponding to ½ the predetermined X-ray detection unit width), the kernel including a target pixel, in units of pixels of the transmission image stored in the storage means by using a predetermined coefficient matrix, thereby calculating a weighted average over the kernel, difference calculating means for calculating a difference between the X-ray intensity of the target pixel of the transmission image stored in the storage means and the weighted average over the kernel of the target pixel which is calculated by the average calculating means, and determining means for comparing the difference calculated by the difference calculating means with predetermined criteria, thereby determining presence/absence of a contaminant in the product to be tested.

Furthermore, according to the present invention, there is also provided a high-selectivity, high-sensitivity contaminant-detecting apparatus for effectively suppressing a false-reject signal, characterized in that the average calculating means has logarithm converting means for converting the X-ray intensity of each of the pixels of the transmission image into a logarithm and calculates the weighted average over the kernel based on the logarithm of the kernel by using the logarithm of the X-ray intensity of each pixel of the transmission image obtained by conversion with the logarithm converting means, and the difference calculating means calculates a difference between the logarithm of the X-ray intensity of the target pixel with the weighted average over the kernel in logarithm of the target pixel.

BRIEF DESCRIPTION OF DRAWINGS

FIG. 1 shows the arrangement of the first embodiment of the present invention;

FIG. 2 shows the arrangement of the second embodiment of the present invention;

FIG. 3 shows a coefficient matrix used in the third embodiment of the present invention;

FIG. 4 shows a coefficient matrix used in the fourth embodiment of the present invention;

FIG. 5 shows a coefficient matrix used in the fifth embodiment of the present invention;

FIG. 6 shows a coefficient matrix used in the sixth embodiment of the present invention;

FIG. 7 shows an example of a coefficient matrix used in the first embodiment of the present invention;

FIGS. 9A and 9B are graphs showing the intensity of a pixel in the A—A section of the transmission image of the product to be tested shown in FIG. 8 and the weighted average over the kernel of the kernel around the pixel simultaneously, in which FIG. 9A shows a case wherein the weighted average over the kernel is calculated by using a 7×7 pixel kernel, and FIG. 9B shows a case wherein the weighted average over the kernel is calculated by using a 3×3 pixel kernel;

FIGS. 12A and 12B are graphs showing the relationship between the intensity and position of the pixel of a transmission image obtained when contaminants with the same material and size are mixed in the central portion and the peripheral portion of a product to be tested, in which FIG. 12A shows a case wherein the intensity of the pixel is not converted into a logarithm, and FIG. 12B shows a case wherein the intensity of the pixel is converted into a logarithm;

FIG. 13 is a graph for explaining the basis for a case wherein the lower limit of a coefficient matrix used in the average calculating means is 7×7;

FIG. 14 is a graph showing for explaining the basis for a case wherein the lower limit of a coefficient matrix used in the average calculating means is 9×9;

FIG. 15 is a graph showing for explaining the basis for a case wherein the lower limit of a coefficient matrix used in the average calculating means is 11×11;

FIG. 16 is a graph showing why the upper limit of a coefficient matrix used in the average calculating means is ½ the width of the X-ray detection unit;

FIG. 17 is a block diagram showing the arrangement of FIGS. 1 and 2 in detail;

FIG. 19 shows a coefficient matrix used in the seventh embodiment of the present invention;

FIG. 20 shows a coefficient matrix used in the eighth embodiment of the present invention;

FIG. 21 shows a coefficient matrix used in the ninth embodiment of the present invention;

FIG. 22 shows a coefficient matrix used in the tenth embodiment of the present invention;

FIG. 23 shows a coefficient matrix used in the eleventh embodiment of the present invention;

FIG. 24 shows a coefficient matrix used in the twelfth embodiment of the present invention;

FIG. 25 shows a coefficient matrix used in the thirteenth embodiment of the present invention;

FIG. 26 shows a coefficient matrix used in the fourteenth embodiment of the present invention;

FIG. 27 shows a coefficient matrix used in the fifteenth embodiment of the present invention; and FIG. 28 shows a coefficient matrix used in the sixteenth embodiment of the present invention.

BEST MODE OF CARRYING OUT THE INVENTION

The outline of a contaminant-detecting apparatus according to the present invention will be described.

In order to achieve the above object, the present inventors examined the algorithm of image processing that used a pixel kernel equal to or larger than 7×7 pixels (or equal to or larger than 9×9 pixels, or equal to or larger than 11×11 pixels) which was not considered in the conventional contaminant-detecting apparatus, as will be described later. The present inventors found that a technique using a large kernel effectively suppressed a false-reject signal caused by the density of the X-ray transmission image of a product to be tested, and accordingly detected a contaminant at high selectivity and with high sensitivity.

The present inventors also found that if the intensity of the pixel was converted into a logarithm before image processing, the contaminant was detected at higher selectivity and with higher sensitivity.

The contaminant-detecting apparatus based on these findings according to the present invention basically comprises a conveying means for conveying a product to be tested, an X-ray source means for radiating X-rays toward the product to be tested, an X-ray detection unit for detecting the X-rays transmitted through the product to be tested, a storage means for storing the two-dimensional distribution of the X-ray intensity detected by the X-ray detection unit as a transmission image, and a processing means for processing the transmission image to determine the presence/absence of a mixed contaminant, wherein the processing means has an average calculating means for performing a sum-of-product operation for a kernel equal to or larger than 7×7 pixels around each pixel of the transmission image by using a predetermined coefficient matrix, thereby calculating a weighted average over the kernel, a difference calculating means for calculating the difference between the intensity of the given pixel and the weighted average over the kernel of this pixel, and a high-selectivity, high-sensitivity determining means for comparing the calculated difference with predetermined criteria, thereby determining the presence/absence of the contaminant.

The function of the contaminant-detecting apparatus according to the present invention having the above arrangement will be described.

Figure 8:
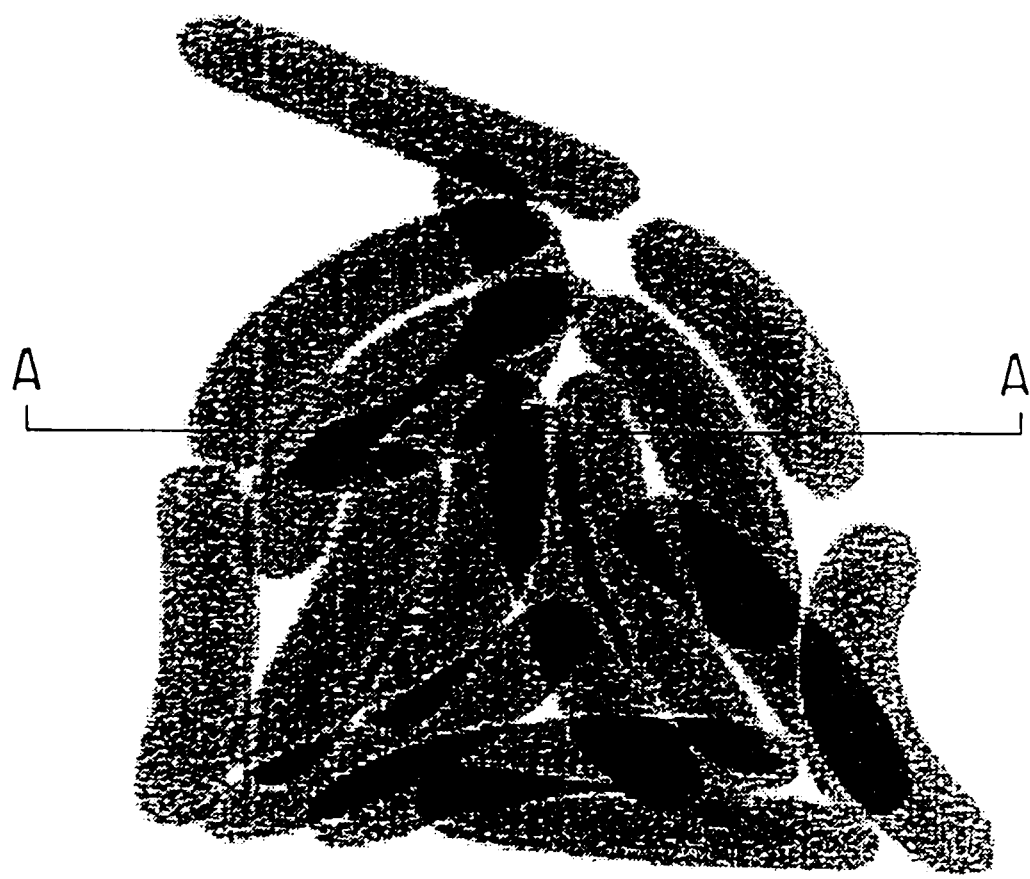
FIG. 8 shows an X-ray transmission image of a product to be tested which contains a contaminant.

More specifically, in the contaminant-detecting apparatus according to the present invention, when the product to be tested which is conveyed by the conveying means passes through the X-rays generated by the X-ray source means, for example, the transmission image as shown in FIG. 8 of the product to be tested can be obtained with the X-ray detection unit.

A contaminant is mixed in the transmission image of the product to be tested shown in FIG. 8.

With the contaminant-detecting apparatus according to the present invention, for example, the weighted average over the kernel of the 7×7 pixel kernel around each pixel of the transmission image obtained in the above manner is calculated with the average calculating means, and thereafter the difference between the intensity of this pixel stored in the storage means and the weighted average over the kernel of this pixel is calculated. The difference between the contaminant signal and the false-reject signal can be enhanced more than with the conventional technique that uses the weighted average over the kernel of the 3×3 pixel kernel.

As a result, according to the present invention, a high-selectivity, high-sensitivity contaminant-detecting apparatus can be realized.

This will be described in detail with reference to FIGS. 9A and 9B.

Figure 9A:
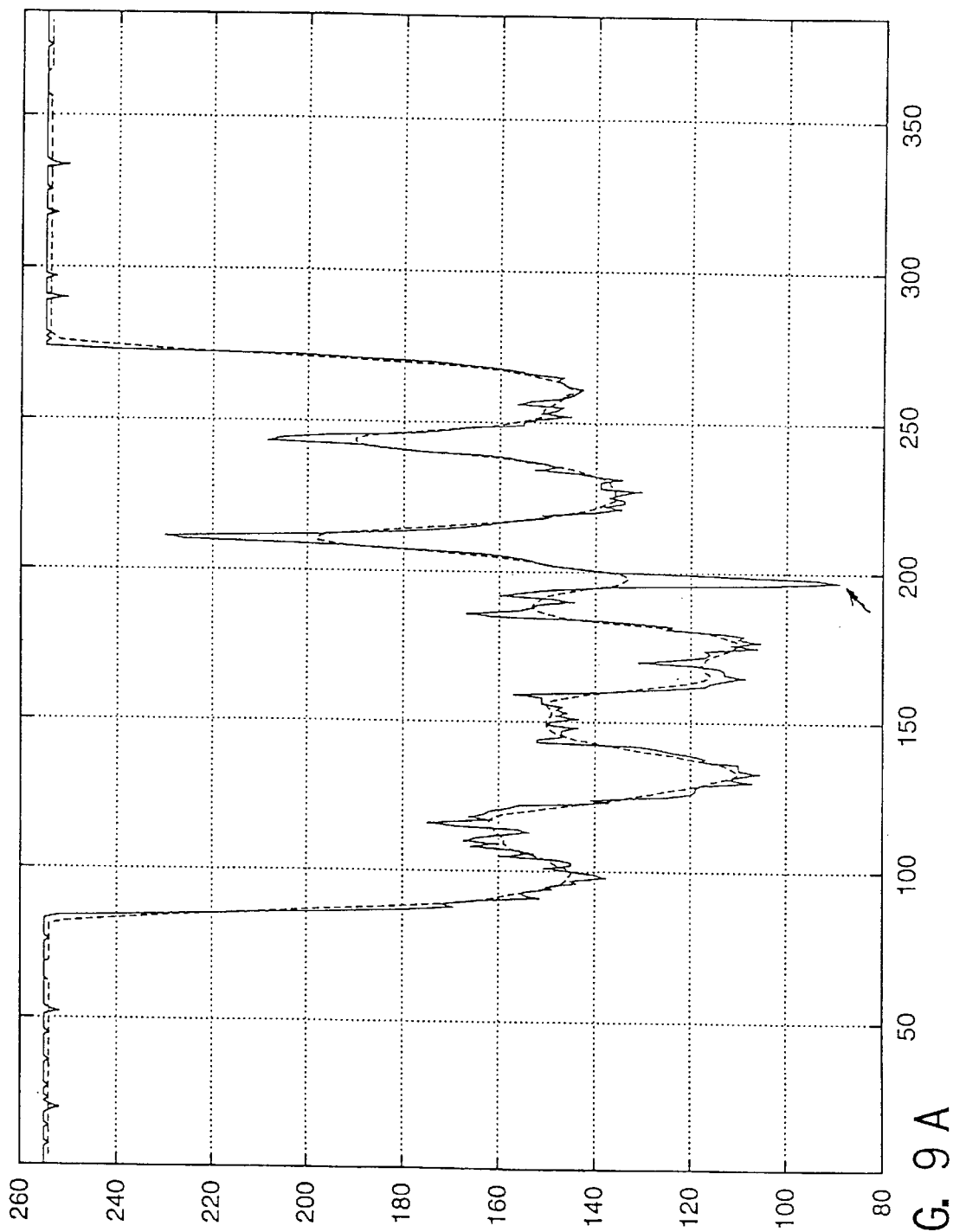

FIG. 9A is a graph showing the intensity of each pixel in the A—A section (pixels in one columns) of the transmission image of the product to be tested shown in FIG. 8 and the weighted average over the kernel of the 7×7 pixel kernel around this pixel simultaneously.

In FIG. 9A, the axis of abscissa indicates the position of the pixel in the transmission image, and the axis of ordinate indicates the intensity of the pixel.

In FIG. 9A, the solid line indicates the intensity of the pixel stored in the storage means, and the broken line indicates the weighted average over the kernel of the 7×7 pixel kernel.

The difference between the intensity indicated by the solid line and that indicated by broken line indicates the difference calculated by the difference calculating means.

A difference at a position where no contaminant is mixed corresponds to a false-reject signal caused by the density of the product to be tested.

In FIG. 9A, the lowest peak indicated by an arrow shows a position where a contaminant is mixed.

The difference between the solid line and the broken line at this contaminant mixed position, i.e., the contaminant signal is considerably larger than signals at other positions, i.e., than false-reject signals.

Figure 9B:
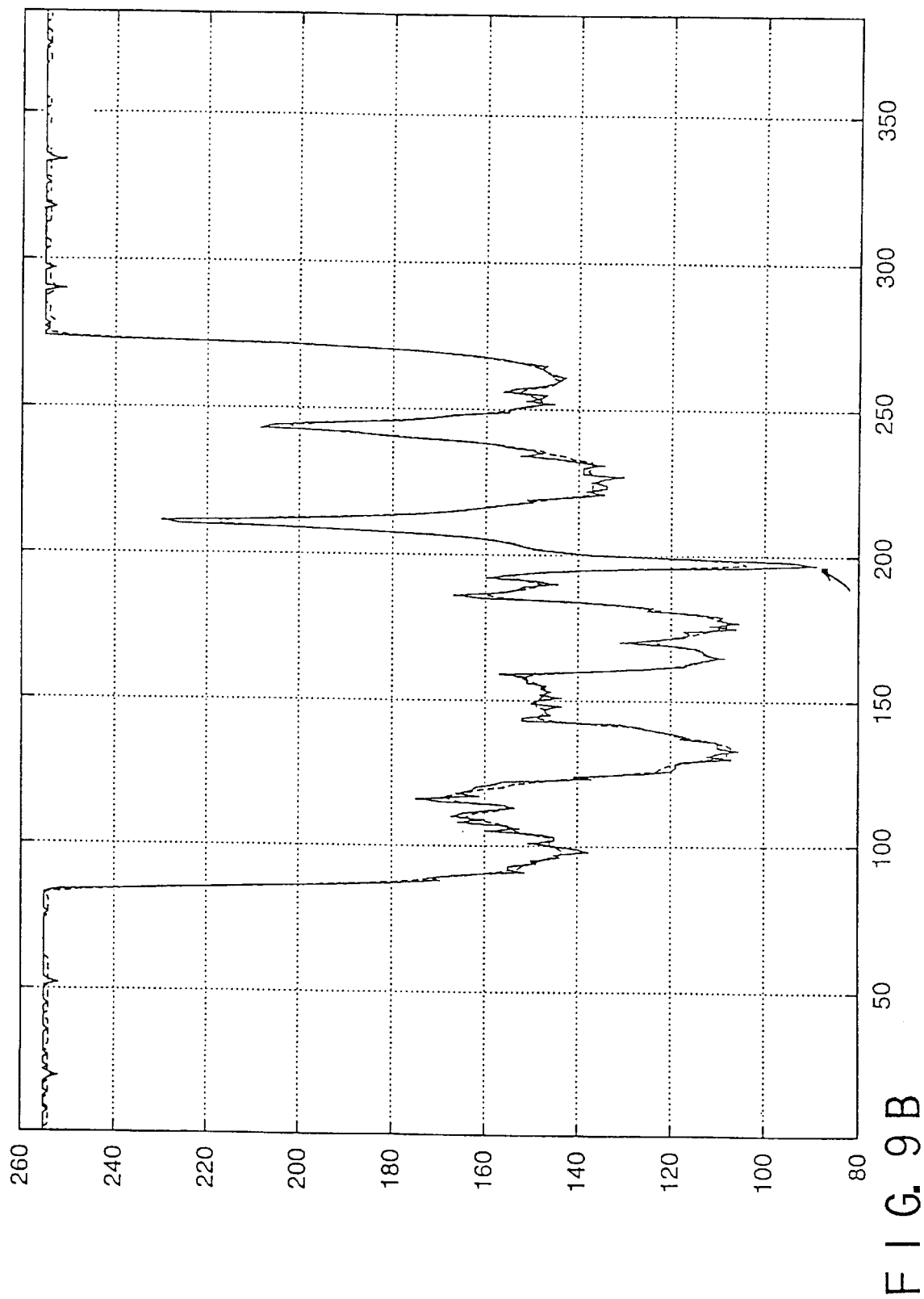

FIG. 9B is a graph showing the intensity of each pixel in the same section as that of FIG. 9A and the weighted average over the kernel of the 3×3 pixel kernel around this pixel simultaneously.

In FIG. 9B, the axis of abscissa indicates the position of the pixel, and the axis of ordinate indicates the intensity of the pixel, in the same manner as in FIG. 9A.

In FIG. 9B, the solid line indicates the intensity of the pixel stored in the storage means, and the broken line indicates the weighted average over the kernel of the 3×3 pixel kernel.

In FIG. 9B, a contaminant signal at a contaminant mixed position indicated by the arrow is very small as compared to the contaminant signal obtained by using the weighted average over the kernel of the 7×7 pixel kernel shown in FIG. 9A, and accordingly the difference between this contaminant signal and the false-reject signal is extremely small.

The above explanation concerns a certain section of the transmission image. In order to study the same issue for the entire transmission image, in FIGS. 10 and 11, the result of image processing is shown three-dimensionally.

Figure 10:
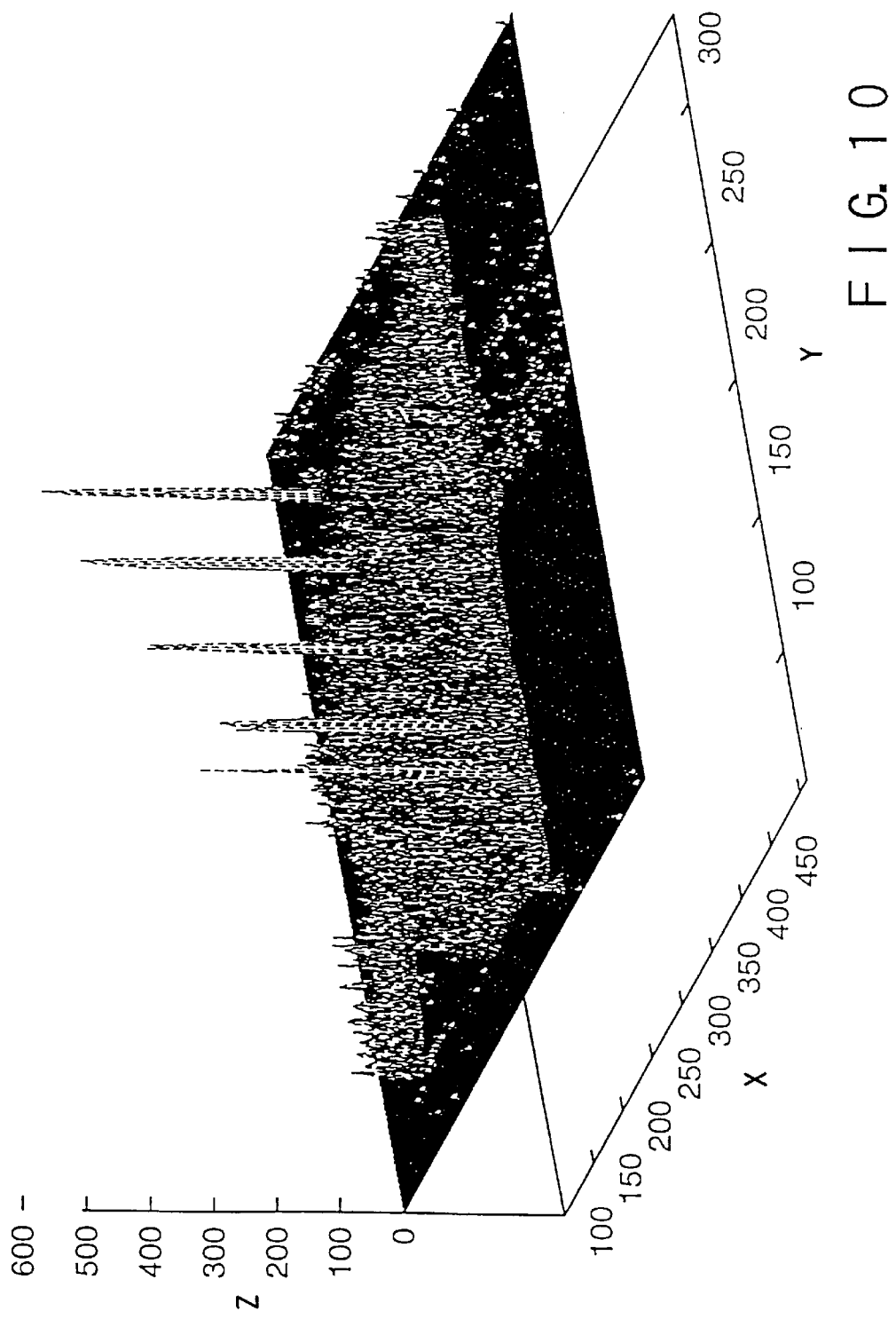
FIG. 10 is a three-dimensional graph showing the output result of image processing that uses the 7×7 pixel kernel of the contaminant-detecting apparatus according to the present invention.
Figure 11:
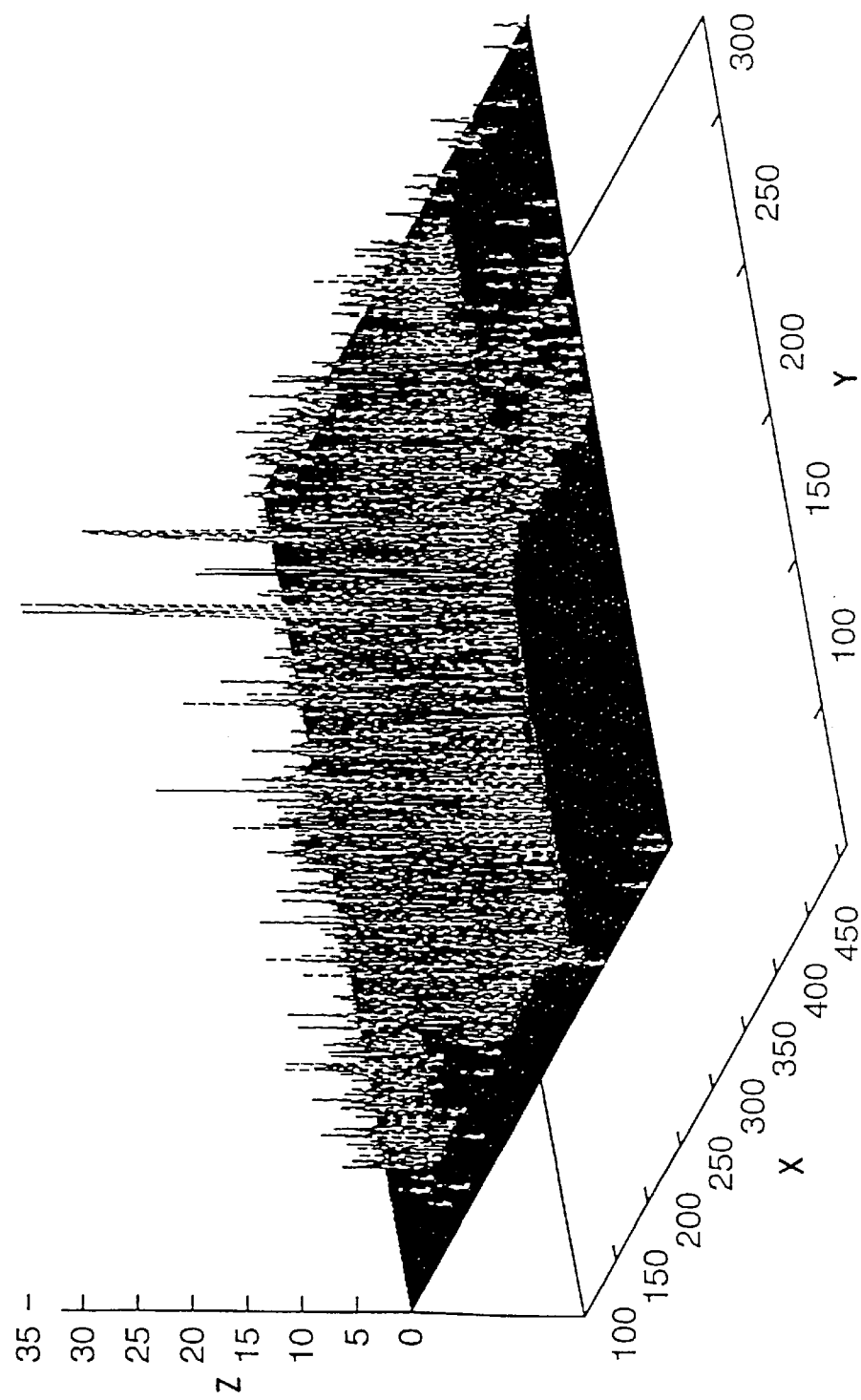
FIG. 11 is a three-dimensional graph showing the output result of image processing that uses the 3×3 pixel kernel of the conventional contaminant-detecting apparatus.

In FIGS. 10 and 11, the X and Y axes indicate the position of the pixel, and the Z axis indicates the difference after image processing of each pixel.

FIG. 10 is a graph showing the output result of image processing that uses the 7×7 pixel kernel of the contaminant-detecting apparatus according to the present invention.

More specifically, FIG. 10 shows the result obtained by calculating, with the average calculating means, the difference between the weighted average over the kernel of the 7×7 pixel kernel around each pixel of the transmission image of the contaminant-containing product to be tested shown in FIG. 8, and the intensity of this pixel stored in the storage means.

In FIG. 10, five peaks projecting at the central portion indicate contaminant signals. All of five mixed contaminants can be detected.

As is apparent from this example, when image processing using the 7×7 pixel kernel is employed, a false-reject signal caused by the density of the transmission image of the product to be tested is largely suppressed as compared to the contaminant signal. Therefore, the contaminant signal is selectively enhanced and stands out.

FIG. 11 is a graph showing the result obtained by performing these series of image processing with the technique of the prior art that calculates the weighted average over the kernel of the 3×3 pixel kernel.

In FIG. 11, although image enhancement is performed for the same transmission image, the difference between the contaminant signal and the false-reject signal becomes small, and the contaminant detection sensitivity is decreased. As a result, with the contaminant-detecting apparatus of the prior art, of five contaminants, only two can be detected.

The products to be tested as the targets of the contaminant-detecting apparatus and contaminants vary, as is enumerated at the end of this specification.

The inventors of the present application performed the comparison described above for the combinations of various types of products to be tested and contaminants, and found that an image processing technique using a kernel equal to or larger than 7×7 more can detect contaminants with higher detection sensitivity than the conventional image processing technique using the 3×3 pixel kernel.

It has become apparent that, as will be described later, the image processing techniques using a kernel equal to or larger than 9×9 pixels, and a kernel equal to or larger than 11×11 pixels were respectively effective for a certain specific combination of the product to be tested and the contaminant.

FIG. 13 is a graph which, in order to explain why the lower limit of the size of coefficient matrix used in the average calculating means that detects a contaminant at high sensitivity is 7×7, shows the relationship between the size of the coefficient matrix and the detection sensitivity as a typical combination among combinations of various types of foods and contaminants.

The axis of abscissa of FIG. 13 indicates the size of the coefficient matrix.

The axis of ordinate of FIG. 13 indicates a detection signal (normalized value) representing the detection sensitivity.

This detection signal is obtained by subtracting a false-reject signal obtained by image processing from a contaminant signal obtained by image processing.

This value is a normalized value calculated statistically based on the variations of the contaminant signals and false-reject signals and the degree of confidence (probability of 99.999998% in this example) of contaminant detection.

The detection signal (normalized value) of FIG. 13 is calculated statistically by image-processing a plurality of processed meat products in which no contaminants are mixed and a plurality of processed meat products in which high-density plastic pieces are mixed.

When the detection signal (normalized value) is larger than 0, statistically, the mixed contaminant can be detected at precision of 99.999998%.

When the detection signal (normalized value) is smaller than 0, the mixed contaminant cannot be detected.

FIG. 13 shows that contaminant detection is possible if a coefficient matrix having a size equal to or larger than 7×7 is used.

FIG. 14 is a graph which, in order to explain why the lower limit of the size of the coefficient matrix used in the average calculating means that detects a contaminant at high sensitivity is 9×9, shows the relationship between the size of the coefficient matrix and the detection sensitivity as an example of a certain specific combination described above among combinations of various types of foods and contaminants.

The axis of abscissa of FIG. 14 indicates the size of the coefficient matrix.

The axis of ordinate of FIG. 14 indicates a detection signal (normalized value) representing the detection sensitivity.

The detection signal (normalized value) of FIG. 14 is calculated statistically by image-processing a plurality of processed meat products in which no contaminants are mixed and a plurality of processed meat products in which small glass pieces are mixed.

When the detection signal (normalized value) is larger than 0, statistically, the mixed contaminant can be detected at precision of 99.87%.

When the detection signal (normalized value) is smaller than 0, the mixed contaminant cannot be detected.

FIG. 14 shows that contaminant detection in a specific combination of, e.g., the processed meat product and a small glass piece mixed in it, as described above, is possible if a coefficient matrix having a size equal to or larger than 9×9 is used.

FIG. 15 is a graph which, in order to explain why the lower limit of the size of the coefficient matrix used in the average calculating means that detects a contaminant at high sensitivity is 11×11, shows the relationship between the size of the coefficient matrix and the detection sensitivity as an example of a certain specific combination described above among combinations of various types of foods and contaminants.

The axis of abscissa of FIG. 15 indicates the size of the coefficient matrix.

The axis of ordinate of FIG. 15 indicates a detection signal (normalized value) representing the detection sensitivity.

The detection signal (normalized value) of FIG. 15 is calculated statistically by image-processing a plurality of processed meat products in which no contaminants are mixed and a plurality of processed meat products in which small stones are mixed.

When the detection signal (normalized value) is larger than 0, statistically, the mixed contaminant can be detected at precision of 99.38%.

When the detection signal (normalized value) is smaller than 0, the mixed contaminant cannot be detected.

FIG. 15 shows that contaminant detection in a specific combination of, e.g., the processed meat product and a small stone mixed in it, as described above, is possible if a coefficient matrix having a size equal to or larger than 11×11 is used.

FIG. 16 is a graph which, in order to explain why the upper limit of the size of the coefficient matrix used in the average calculating means that detects a contaminant at high sensitivity is (a pixel count corresponding to ½ the width of the X-ray detection unit)×(a pixel count corresponding to ½ the width of the X-ray detection unit), shows the relationship between the size of the coefficient matrix and the detection sensitivity as an example of a typical combination among combinations of various types of foods and contaminants.

The axis of abscissa of FIG. 16 indicates, in length (mm), the size of the coefficient matrix used by an average calculation unit 7 when the width of 1 pixel of the X-ray detection unit is 1 mm.

For example, 50 mm on the axis of abscissa of FIG. 17 indicates the matrix size of 50×50.

The axis of ordinate of FIG. 16 indicates a detection signal (normalized value) representing the detection sensitivity.

The detection signal (normalized value) of FIG. 16 is calculated statistically by image-processing a plurality of processed meat products in which no contaminants are mixed and a plurality of processed meat products in which small metal pieces are mixed.

When the detection signal (normalized value) is larger than 0, statistically, the mixed contaminant can be detected at precision of 99.9999999%.

When the detection signal (normalized value) is smaller than 0, the mixed contaminant cannot be detected.

It is apparent from FIG. 16 that when the size of coefficient matrix is equal to or smaller than 50 mm (½ the width of the X-ray detection unit), a contaminant detection is possible.

As described above by using actual detection examples as compared to prior arts, the contaminant-detecting apparatus according to the present invention, which employs image processing using a pixel kernel equal to or larger than 7×7 pixels and equal to or smaller than (a pixel count corresponding to ½ the width of the X-ray detection unit)×(a pixel count corresponding to ½ the width of the X-ray detection unit), can clearly discriminate a contaminant signal from a false-reject signal at high selectivity.

As a consequence, the contaminant-detecting apparatus according to the present invention has higher sensitivity than that of the contaminant-detecting apparatus of the prior art which has image processing using 3×3 pixels.

The embodiments of the present invention based on the above outline will be described.

FIG. 1 shows the arrangement of the first embodiment of the present invention.

As shown in FIG. 1, the contaminant-detecting apparatus of this embodiment is constituted by a belt 2 serving as a conveying means for conveying a product 1 to be tested, e.g., food, an X-ray source 3 for radiating X-rays to the product 1 to be tested, an X-ray detection unit 4 for detecting the X-rays transmitted through the product 1 to be tested, a storage unit 5 for storing the two-dimensional distribution of the X-ray intensity detected by the X-ray detection unit 4 as a transmission image, an average calculation unit 7 for performing a sum-of-product operation for a kernel equal to or larger than 7×7 pixels around each pixel of the transmission image by using a predetermined coefficient matrix to calculate the weighted average over the kernel, a difference calculation unit 8 for calculating the difference between the intensity of the given pixel and the weighted average over the kernel of this pixel, and a determination unit 9 for comparing the calculated difference with predetermined criteria to determine the presence/absence of the contaminant.

Of these constituent components, the average calculation unit 7, the difference calculation unit 8, and the determination unit 9 constitute a processing unit 6 having a central processing unit (CPU) or the like.

The products to be tested as the target of the present invention as well as detectable contaminants are enumerated at the end of this specification.

The principle of contaminant detection by the contaminant-detecting apparatus having the above arrangement according to the first embodiment of the present invention is as follows.

As shown in FIG. 1, when the product 1 to be tested is conveyed with the belt 2 serving as the conveying means and passes under the X-ray source 3, X-rays having an intensity corresponding to the X-ray transmission coefficient of the product 1 to be tested are transmitted through the product 1 to be tested.

The X-rays which are transmitted through the product 1 to be tested are continuously detected by the X-ray detection unit 4.

The intensity of X-rays detected by the X-ray detection unit 4 is stored in the storage unit 5.

Hence, a transmission image as the two-dimensional distribution of the transmitted X-ray intensity is obtained.

According to this apparatus, the transmission image obtained in this manner is subjected to predetermined image processing with the processing unit 6 constituted by the average calculation unit 7, the difference calculation unit 8, and the determination unit 9, to determine the presence/absence of a contaminant that might be mixed in the product 1 to be tested.

This image processing will be described in more detail. The transmission image stored in the storage unit 5 is sent to the average calculation unit 7. The average calculation unit 7 calculates the weighted average over the kernel of the 7×7 pixel kernel around the given pixel by using, e.g., the coefficient matrix as shown in FIG. 7.

The weighted average over the kernel is calculated by the average calculation unit 7 in accordance with the following procedure.

More specifically, the intensities of the respective pixels of 7×7 pixels=49 pixels are multiplied by the corresponding coefficients of the coefficient matrix. All the products are summed, and the sum is divided by 8, which is the sum of the coefficients.

The difference calculation unit 8 calculates the difference between the weighted average over the kernel obtained in this manner and the intensity of the given pixel.

This difference is calculated for all the pixels, thereby finally obtaining the processing result.

Finally, the determination unit 9 compares the value of each pixel of the image of this processing result with the predetermined criteria. When the comparison result shows that a pixel exceeding the criteria exists, it is determined that a contaminant is mixed.

In the above description, examples of the technique of setting the criteria include a technique wherein the transmission image of one product to be tested in which no contaminant is mixed is processed by the average calculation unit 7 and difference calculation unit 8, and the maximum of the values indicating the processing results of all the pixels, or a value obtained by adding a margin to the maximum, is set as the criteria.

As the technique of setting the criteria, other than the technique using the maximum value, as described above, a technique of statistically determining the criteria is also available.

More specifically, according to this statistic technique, a plurality of maximum values are obtained by performing the above technique but by using a plurality of products to be tested in which no contaminants are mixed. The average and variance of the maximum values are calculated, and criteria are obtained from the variance by considering the margin.

The second embodiment of the present invention will be described with reference to FIG. 2.

The difference between the second and first embodiments is that in the second embodiment a logarithm converting unit 10 is added to a processing unit 6.

As shown in FIG. 2, when a product 1 to be tested is conveyed with a belt 2 serving as the conveying means and passes under an X-ray source 3, X-rays corresponding to the X-ray transmission coefficient of the product 1 to be tested are transmitted through the product 1 to be tested.

The X-rays which are transmitted through the product 1 to be tested are continuously detected by an X-ray detection unit 4.

The intensity of X-rays detected by the X-ray detection unit 4 is stored in a storage unit 5.

Hence, a transmission image as the two-dimensional distribution of the transmitted X-ray intensity is obtained.

According to this apparatus, the transmission image obtained in this manner is subjected to predetermined image processing with the processing unit 6 constituted by a logarithm converting unit 10, an average calculation unit 7, a difference calculation unit 8, and a determination unit 9, to determine the presence/absence of a contaminant that might be mixed in the product 1 to be tested.

This image processing will be described in more detail. The transmission image stored in the storage unit 5 is sent to the logarithm converting unit 10. The values of all the pixels are individually converted into logarithms and are sent to the average calculation unit 7.

The average calculation unit 7 calculates the weighted average over the kernel of the 7×7 pixel kernel around the given pixel by using, e.g., the coefficient matrix having contaminants as shown in FIG. 7.

The weighted average over the kernel is calculated in accordance with the following procedure.

More specifically, the logarithm-converted values of the intensities of the respective ones of the 7×7 pixels=49 pixels are multiplied by the corresponding coefficients of the coefficient matrix. All the products are summed, and the sum is divided by 8, which is the sum of the coefficients.

The difference calculation unit 8 calculates the difference between the weighted average over the kernel obtained in this manner and the logarithm of the intensity of the given pixel.

The difference between the weighted average over the kernel, which has been converted into the logarithm, and the logarithm of the intensity of the given pixel is calculated for all of the pixels, thereby finally obtaining the processing result.

Finally, the determination unit 9 compares the value of each pixel (logarithm) of this processing result with predetermined criteria. When the comparison result shows that a pixel exceeding the criteria exists, it is determined that a contaminant is mixed.

The effect of logarithm conversion performed by the logarithm converting unit 10 will be described with reference to FIGS. 12A and 12B.

Figure 12A:
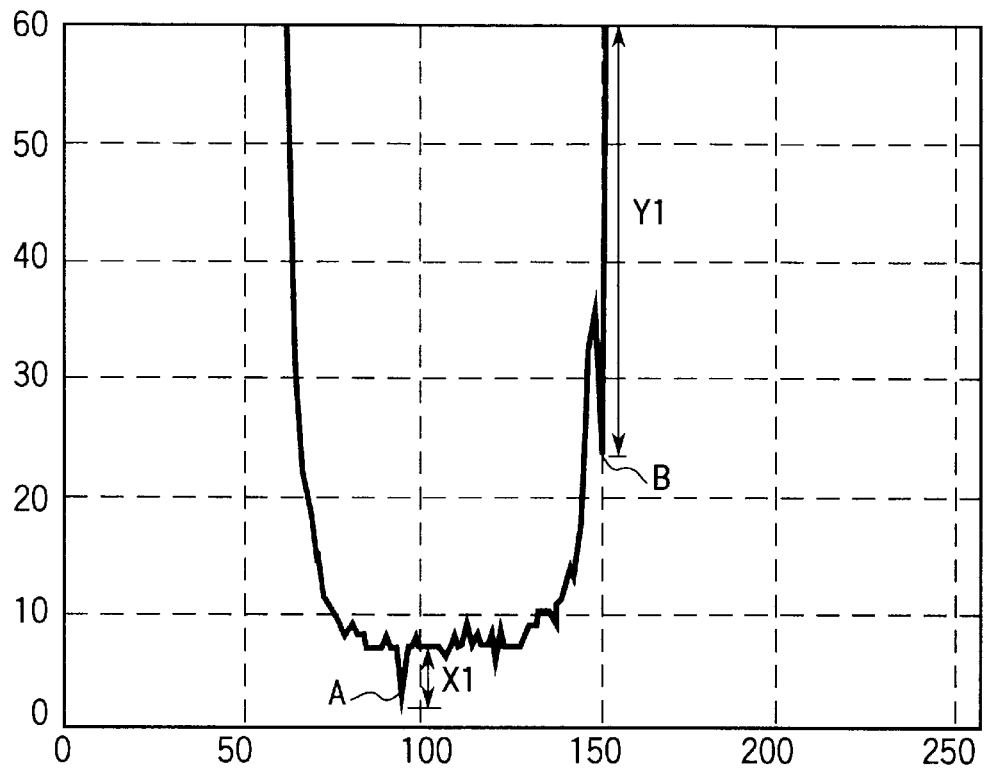
Figure 12B:
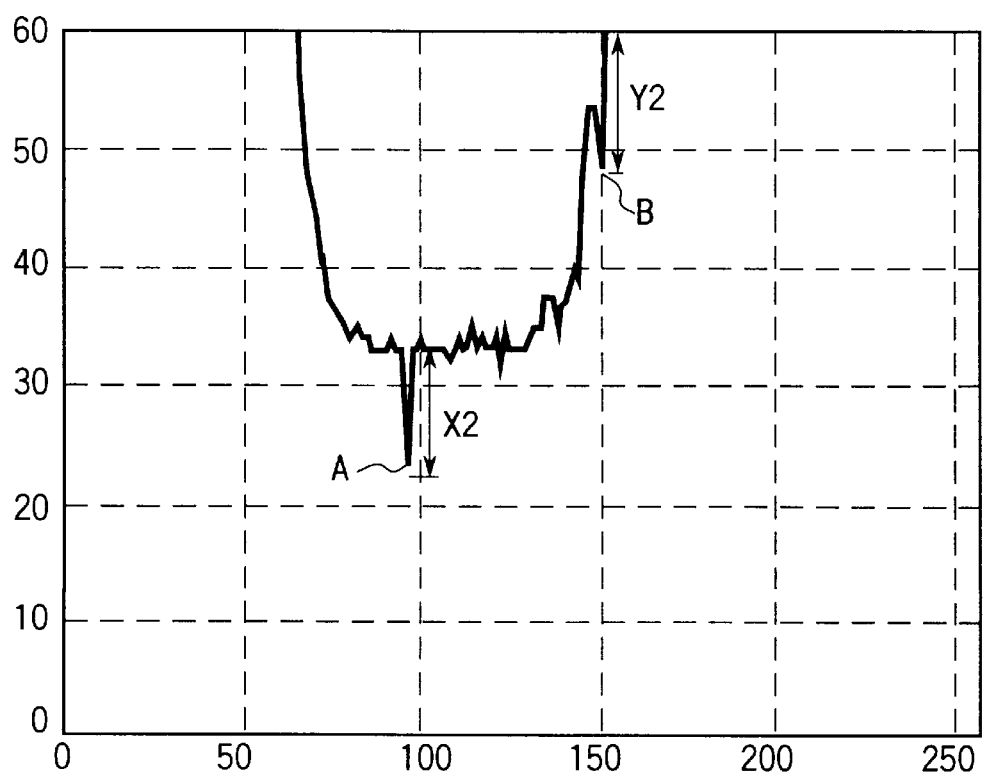

FIGS. 12A and 12B are graphs showing the intensity of the pixel of a certain section of a transmission image obtained when contaminants with the same material and size are mixed in two portions, i.e., the central portion and the peripheral portion of a product to be tested.

The axis of abscissa of each of FIGS. 12A and 12B indicates the position of the pixel, the axis of ordinate of FIG. 12A indicates the intensity of the pixel, and the axis of ordinate of FIG. 12B indicates the logarithm of the intensity of the pixel.

Referring to FIG. 12A, the position indicated by A at the central portion indicates the intensity of X-rays which are transmitted through the product to be tested and the contaminant that overlap each other. The contaminant signal is X1, from which the intensity of X-rays that are transmitted through only the product to be tested has been subtracted.

At the position indicated by B at the peripheral portion, the intensity of X-rays which are transmitted through only the product to be tested is substantially not included, and the contaminant signal in most part accounts for the value.

The intensity of this contaminant signal is represented by Y1.

More specifically, in FIG. 12A, when the two contaminant signals indicated at the positions A and B are compared, the magnitude of the contaminant signal differs depending on the position where the contaminant is mixed.

In contrast to this, FIG. 12B shows the result obtained by converting the intensity of each pixel into a logarithm by the logarithm converting unit 10. The position indicated by A at the central position shows the logarithm of the intensity of X-rays, although the product to be tested and the contaminant overlap, and the contaminant signal is X2, from which the logarithm of the intensity of X-rays of the product to be tested has been subtracted.

At the position indicated by B at the peripheral portion, the logarithm of the intensity of X-rays of the product to be tested is substantially not included, and the contaminant signal in most part accounts for the signal. The intensity of the contaminant signal is Y2.

More specifically, in FIG. 12B, when the two contaminant signals X2 and Y2 indicated at the positions A and B are compared, they are completely equal.

As a result, when logarithm conversion is performed, the contaminant signal is not influenced by the product to be tested at all, and is free from any difference depending on the mixed position of the contaminant.

As is apparent from FIG. 12B, when the intensity of X-rays of the product to be tested is suppressed by logarithm conversion, the contaminant signal is relatively enhanced.

In this manner, the contaminant-detecting apparatus that performs logarithm conversion can relatively enhance the contaminant signal with respect to the intensity of X-rays of the product to be tested.

This suggests that the contaminant signal can be relatively enhanced even when compared to the false-reject signal arising from the density of the transmission image of the product to be tested as well. Consequently, the contaminant-detecting apparatus performs image processing highly selectively, so that highly sensitive contaminant detection becomes possible.

FIG. 17 shows the arrangements of the embodiments shown in FIGS. 1 and 2 in more detail.

Referring to FIG. 17, note that portions that have the same arrangement as those of FIGS. 1 and 2 are denoted by the same reference numerals as in FIGS. 1 and 2, and a description thereof will be omitted.

More specifically, in this practical contaminant-detecting apparatus, the X-ray detection unit 4 has a linear array 4a which is disposed under the belt 2 which conveys the product 1 to be tested in the direction perpendicularly intersecting the surface of the sheet of FIG. 17, and has a predetermined number of pixels arranged in the direction perpendicularly intersecting the conveying direction of the product 1 to be tested, an amplifier 4b for amplifying the electric signal sent from the linear array 4a, a sample-and-hold circuit (S/H) 4c for sampling and holding an output from the amplifier 4b, and an analog-to-digital converter (A/D) 4d for analog-to-digital converting an output from the S/H 4c.

The X-ray source 3 radiates, with a certain width, X-rays in the direction perpendicularly intersecting the conveying direction of the product 1 to be tested. The X-rays are transmitted through the product 1 to be tested and the belt 2, and are input to the linear array 4a. The linear array 4a is an X-ray detection unit which converts the input transmission X-rays into a one-line electric signal by scanning them in units of pixels, and outputs the electric signal.

For example, the linear array 4a has 128 pixels. The size of each pixel is 1 mm×1 mm. The scan speed is 350 scan/sec. The convey speed of the belt 2 is 20 m/min.

Data A/D-converted by the A/D 4d, i.e., output data from the X-ray detection unit 4 is fetched by a CPU (A) 11a of a control unit 11 that controls the whole apparatus.

The CPU (A) 11a transfers the fetched data to a CPU (B) 6a of the image processing unit 6 at high speed through an interface circuit (I/F) 6b.

The CPU (B) 6a performs predetermined image processing as will be described later, and sends back the image processing result to the CPU (A) 11a through the I/F 6b.

The CPU (A) 11a displays the image processing result (X-ray transmission image) on a monitor screen 11d and outputs a contaminant detection signal.

The CPU (A) 11a of the control unit 11 that controls the whole apparatus controls the whole apparatus (the X-ray detection unit 4, a conveyor controller/driver 12, and the image processing unit 6), and has an internal memory 5 for storing data.

An input button is arranged on an operation screen 11c of the control unit 11. The user operates the input button while monitoring this screen, thereby controlling the CPU (A) 11a.

A memory card 11b of the control unit 11 stores setting data for setting various types of conditions that are required by the apparatus as a whole, and transmission image data to be saved.

The conveyor controller/driver 12 turns on/off the belt 2 based on a control signal supplied from the CPU (A) 11a through an I/F 13, and controls the convey speed to a predetermined speed.

The CPU (B) 6a of the image processing unit 6 performs predetermined image processing as will be described later based on the image processing program stored in a flash memory 6c, and has an internal memory (not shown) for storing data during processing.

Figure 18:
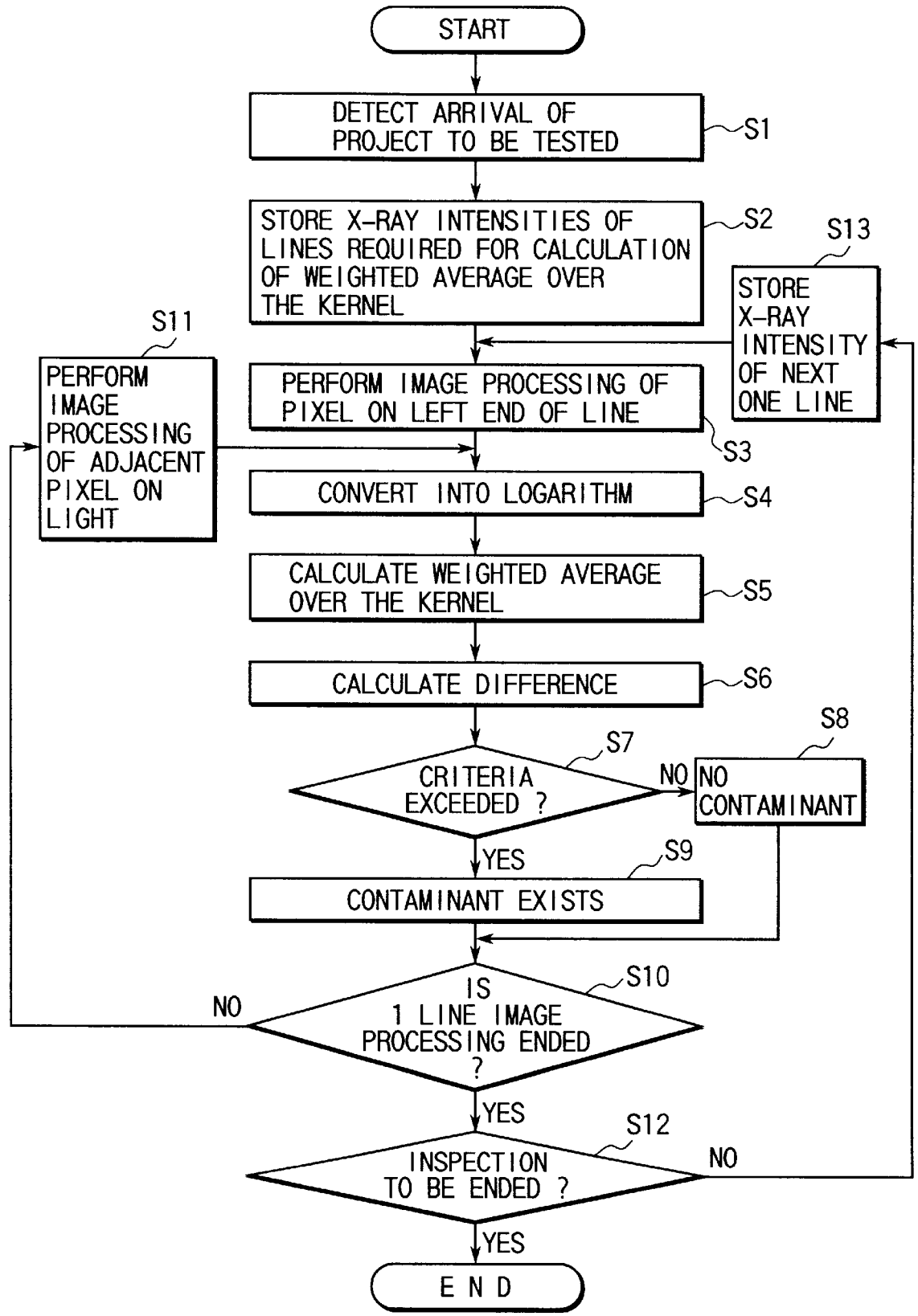
FIG. 18 is a flow chart for explaining the operation of FIG. 17.

FIG. 18 is a flow chart for explaining the image processing operation which is performed for contaminant detection with the contaminant-detecting apparatus having the arrangement as shown in FIG. 17 described above.

As described above, this image processing is performed in accordance with the image processing program stored in the flash memory 6c.

The CPU (B) 6a fetches the output data from the X-ray detection unit 4 through the internal memory 5 of the CPU (A) 11a, to detect, based on this data, that the product 1 to be tested has arrived at a predetermined position on the belt 2 as shown in FIG. 17 (step S1).

When arrival of the product 1 to be tested is detected in this manner, the CPU (B) 6a stores the X-ray intensities of lines required for calculation of the weighted average over the kernel, in the internal memory (not shown) based on the output data from the X-ray detection unit 4 which is fetched first (step S2).

For example, the required lines are 7 lines when the kernel size is 7×7; 9 lines when the kernel size is 9×9; and 11 lines when the kernel size is 11×11.

The X-ray intensities of the predetermined lines stored in this manner are image-processed by the CPU (B) 6a sequentially concerning each pixel starting from one on the left end of each line (step S3).

In this image processing, first, the CPU (B) 6a converts the X-ray intensities into logarithms in units of pixels (step S4).

Subsequently, the CPU (B) 6a calculates the weighted average over the kernel based on the logarithms of the X-ray intensities in units of pixels (step S5), and calculates the difference between the calculated weighted average over the kernel and the original pixel data (step S6).

The CPU (B) 6a then examines whether the difference calculated in the above manner exceeds the criteria, thereby determining the presence/absence of a contaminant that might be mixed (step S7).

If the difference does not exceed the criteria, the CPU (B) 6a determines that no contaminant exists, and advances from step S8 to the processing operation of step S10 (to be described later).

If the difference exceeds the criteria, the CPU (B) 6a determines that a contaminant is mixed in the product 1 to be tested, and advances from step S9 to the processing of step S10 (to be described later).

In step S10, the CPU (B) 6a determines whether one-line image processing is ended.

If the CPU (B) 6a determines in step S10 that one-line image processing is not ended yet, it advances to the processing of step S11, and image-processes a pixel adjacent on the right of the pixel that has been processed.

If the CPU (B) 6a determines in step S10 that one-line image processing is ended, it advances to the processing of step S12 to determine whether the inspection is to be continued.

If the CPU (B) 6a determines in step S12 that the inspection is to be continued, it newly stores one-line X-ray intensities in the internal memory in order to calculate the weighted average over the kernel of the next one line (step S13), and performs the processing of steps S3 to S11 described above.

If the CPU (B) 6a determines in step S12 that the inspection is not to be continued, it ends the processing.

The third embodiment of the present invention will be described.

In the third embodiment, the arrangement of the apparatus is the same as that of the first or second embodiment, and is different from that of the first or second embodiment in the coefficient matrix which is used in an average calculation unit 7 that calculates the weighted average over the kernel.

As shown in FIG. 3, in the coefficient matrix of the average calculation unit 7 that calculates the weighted average over the kernel used in this embodiment, all of the 7×7=49 coefficients are 1.

More specifically, in the average calculation unit 7, the intensities of all the 49 pixels are multiplied by the coefficients 1 of the coefficient matrix. All the products are summed, and the sum is divided by 49, which is the sum of the coefficients.

When this coefficient matrix is used, the average calculation unit 7 calculates the weighted average over the kernel by using the intensities of all the pixels around the given pixel in the 7×7 pixel kernel.

As a result, the contaminant-detecting apparatus for calculating the weighted average over the kernel as described above can decrease a false-reject signal owing to the density of the transmission image of a product to be tested which is equal to or smaller than 7×7 pixels, and can improve the contaminant detection sensitivity.

The fourth embodiment of the present invention will be described.

In the fourth embodiment, the arrangement of the apparatus is the same as that of the first or second embodiment, and is different from that of the first or second embodiment in the coefficient matrix which is used in an average calculation unit 7 that calculates the weighted average over the kernel.

As shown in FIG. 4, in the coefficient matrix of the average calculation unit 7 that calculates the weighted average over the kernel used in this embodiment, the 49 elements of the coefficient matrix form a checker-board pattern in which the elements of each row are alternately 1 and 0 and the elements of each column are alternately 1 and 0.

More specifically, in the average calculation unit 7, the intensities of the 49 pixels are multiplied by the corresponding coefficients of the coefficient matrix. All the products are summed, and the sum is divided by 25, which is the sum of the coefficients.

When this coefficient matrix is used, the average calculation unit 7 calculates the weighted average over the kernel based on the intensities of every other pixels around the given pixel in the 7×7 pixel kernel.

As a consequence, the contaminant-detecting apparatus for calculating the weighted average over the kernel as described above can decrease a false-reject signal attributed to the density of the transmission image of a product to be tested which is equal to or smaller than 7×7 pixels, and can improve the contaminant detection sensitivity.

In this case, in the actual calculation, when the coefficient of the coefficient matrix is 0, no calculation is performed, so that the number of times the sum-of-product operation is performed to calculate the average can be reduced.

More specifically, in this embodiment, about half the coefficients are 0. Since the number of times of the calculating operation can be reduced to about half that of the first embodiment, higher-speed processing can be performed accordingly.

The fifth embodiment of the present invention will be described.

In the fifth embodiment, the arrangement of the apparatus is the same as that of the first or second embodiment, and is different from that of the first or second embodiment in the coefficient matrix which is used in an average calculation unit 7 that calculates the weighted average over the kernel.

As shown in FIG. 5, in the coefficient matrix of the average calculation unit 7 that calculates the weighted average over the kernel used in this embodiment, of the 49 elements of the coefficient matrix, all the elements of the first and last rows are 1, all the elements of the first and last columns are 1, and all the remaining elements are 0.

More specifically, in the average calculation unit 7, the intensities of the 49 pixels are multiplied by the corresponding coefficients of the coefficient matrix. All the products are summed, and the sum is divided by 24, which is the sum of the coefficients.

When this coefficient matrix is used, the average calculation unit 7 calculates the weighted average over the kernel based on the intensities of the pixels on the circumference of the 7×7 pixel kernel.

Consequently, the contaminant-detecting apparatus for calculating the weighted average over the kernel as described above can selectively decrease a false-reject signal resulting from fluctuations in density of a kernel, in a product to be tested, with sides each substantially having a length equal to about 7 pixels, and can improve the contaminant detection sensitivity.

In fine, this embodiment is particularly effective for a special application where a contaminant with sides each having a length equal to about 7 pixels is to be detected.

In this case, in the actual calculation, when the coefficient of the coefficient matrix is 0, no calculation is performed, so that the number of times the sum-of-product operation is performed to calculate the average can be reduced.

More specifically, in this embodiment, about half the coefficients are 0. Since the number of times of the calculating operation can be reduced to about half that of the first embodiment, higher-speed processing can be performed accordingly.

The sixth embodiment of the present invention will be described.

In the sixth embodiment, the arrangement of the apparatus is the same as that of the first or second embodiment, and is different from that of the first or second embodiment in the coefficient matrix which is used in an average calculation unit 7 that calculates the weighted average over the kernel.

As shown in FIG. 6, in the coefficient matrix of the average calculation unit 7 that calculates the weighted average over the kernel used in this embodiment, of the 49 elements of the coefficient matrix, those corresponding to the pixels on the circle having a diameter equal to 7 pixels are 1, and all of those corresponding to the remaining pixels are 0.

More specifically, in the average calculation unit 7, the intensities of the 49 pixels are multiplied by the corresponding coefficients of the coefficient matrix. All the products are summed, and the sum is divided by 16, which is the sum of the coefficients.

When this coefficient matrix is used, the average calculation unit 7 calculates the weighted average over the kernel based on the intensities of the pixels on the circle having a diameter equal to 7 pixels.

As a result, the contaminant-detecting apparatus for calculating the weighted average over the kernel as described above can selectively decrease a false-reject signal resulting from fluctuations in density in a kernel having a diameter equal to about 7 pixels, and can improve the contaminant detection sensitivity.

In fine, this embodiment is particularly effective for a special application where a contaminant having a size almost equal to the diameter is to be detected.

In this case, in the actual calculation, when the coefficient of the coefficient matrix is 0, no calculation is performed, so that the number of times the sum-of-product operation is preformed to calculate the average can be reduced.

More specifically, in this embodiment, about $2/3$ the coefficients are 0, and about $1/3$ the coefficients that remain are 1. Since the number of times of the calculating operation can be reduced to about $1/3$ that of the first embodiment, higher-speed processing can be performed accordingly.

The seventh embodiment of the present invention will be described.

In the seventh embodiment, the arrangement of the apparatus is the same as that of the first or second embodiment, and is different from that of the first or second embodiment in the coefficient matrix which is used in an average calculation unit 7 that calculates the weighted average over the kernel.

The average calculation unit 7 calculates the weighted average over the kernel of a 9×9 pixel kernel around the given pixel by using, e.g., a coefficient matrix having coefficients as shown in FIG. 19.

The calculation of the weighted average over the kernel is performed in accordance with the following procedure.

More specifically, the logarithms of the intensities of the respective ones of the 9×9 pixels=81 pixels are multiplied by the corresponding coefficients of the coefficient matrix. All the products are summed, and the sum is divided by 20, which is the sum of the coefficients.

When this coefficient matrix is used, the average calculation unit 7 calculates the weighted average over the kernel by using the intensities of all the pixels around the given pixel in a 9×9 pixel kernel.

As a result, the contaminant-detecting apparatus for calculating the weighted average over the kernel as described above can decrease a false-reject signal resulting from fluctuations in density in a kernel equal to about 9×9 pixels, and effectively detects a specific contaminant which can be mixed in a specific product to be tested, as described earlier with reference to FIG. 14, so that the contaminant detection sensitivity is improved.

The eighth embodiment of the present invention will be described.

In the eighth embodiment, the arrangement of the apparatus is the same as that of the first or second embodiment, and is different from that of the first or second embodiment in the coefficient matrix which is used in an average calculation unit 7 that calculates the weighted average over the kernel.

As shown in FIG. 20, in the coefficient matrix of the average calculation unit 7 that calculates the weighted average over the kernel used in this embodiment, all of the 9×9=81 elements are 1.

More specifically, in the average calculation unit 7, the intensities of all the 81 pixels are multiplied by the coefficients 1 of the coefficient matrix. All the products are summed, and the sum is divided by 81, which is the sum of the coefficients.

When this coefficient matrix is used, the average calculation unit 7 calculates the weighted average over the kernel by using the intensities of all the pixels around the given pixel in the 9×9 pixel kernel.

As a consequence, the contaminant-detecting apparatus for calculating the weighted average over the kernel as described above can decrease a false-reject signal resulting from fluctuations in density of a kernel equal to about 9×9 pixels, and can improve the contaminant detection sensitivity.

The ninth embodiment of the present invention will be described.

In the ninth embodiment, the arrangement of the apparatus is the same as that of the first or second embodiment, and is different from that of the first or second embodiment in the coefficient matrix which is used in an average calculation unit 7 that calculates the weighted average over the kernel.

As shown in FIG. 21, in the coefficient matrix of the average calculation unit 7 that calculates the weighted average over the kernel used in this embodiment, of the 9×9=81 elements of the coefficient matrix, the elements of each row are alternately 1 and 0 and the elements of each column are alternately 1 and 0, thus forming a checker-board pattern.

More specifically, in the average calculation unit 7, the intensities of the 81 pixels are multiplied by the corresponding coefficients of the coefficient matrix. All the products are summed, and the sum is divided by 41, which is the sum of the coefficients.

When this coefficient matrix is used, the average calculation unit 7 calculates the weighted average over the kernel based on the intensities of every other pixels around the given pixel in the 9×9 pixel kernel.

Therefore, the contaminant-detecting apparatus for calculating the weighted average over the kernel as described above can decrease a false-reject signal ascribed to fluctuations in density of a kernel equal to about 9×9 pixels, and can improve the contaminant detection sensitivity.

In this case, in the actual calculation, when the coefficient of the coefficient matrix is 0, no calculation is performed, so that the number of times the sum-of-product operation is performed to calculate the average can be reduced.

More specifically, in this embodiment, about half the coefficients are 0. Since the number of times of the calculating operation can be reduced to about half that of the seventh embodiment, higher-speed processing can be performed accordingly.

The tenth embodiment of the present invention will be described.

In the tenth embodiment, the arrangement of the apparatus is the same as that of the first or second embodiment, and is different from that of the first or second embodiment in the coefficient matrix which is used in an average calculation unit 7 that calculates the weighted average over the kernel.

As shown in FIG. 22, in the coefficient matrix of the average calculation unit 7 that calculates the weighted average over the kernel used in this embodiment, of the 9×9=81 elements of the coefficient matrix, all the elements of the first and last rows are 1, all the elements of the first and last columns are 1, and all the remaining elements are 0.

More specifically, in the average calculation unit 7, the intensities of the 81 pixels are multiplied by the corresponding coefficients of the coefficient matrix. All the products are summed, and the sum is divided by 32, which is the sum of the coefficients.

When this coefficient matrix is used, the average calculation unit 7 calculates the weighted average over the kernel based on the intensities of the pixels on the circumference of the 9×9 pixel kernel.

Hence, the contaminant-detecting apparatus for calculating the weighted average over the kernel as described above can selectively decrease a false-reject signal due to fluctuations in density of a kernel, in a product to be tested, with sides each substantially having a length equal to about 9 pixels, and can improve the contaminant detection sensitivity.

In fine, this embodiment is particularly effective for a special application where a contaminant with sides each having a length equal to about 9 pixels is to be detected.

In this case, in the actual calculation, when the coefficient of the coefficient matrix is 0, no calculation is performed, so that the number of times the sum-of-product operation is performed to calculate the average can be reduced.

More specifically, in this embodiment, about half the coefficients are 0. Since the number of times of the calculating operation can be reduced to about half that of the seventh embodiment, higher-speed processing can be performed accordingly.

The eleventh embodiment of the present invention will be described.

In the eleventh embodiment, the arrangement of the apparatus is the same as that of the first or second embodiment, and is different from that of the first or second embodiment in the coefficient matrix which is used in an average calculation unit 7 that calculates the weighted average over the kernel.

As shown in FIG. 23, in the coefficient matrix of the average calculation unit 7 that calculates the weighted average over the kernel used in this embodiment, of the 9×9=81 elements of the coefficient matrix, those corresponding to the pixels on the circle having a diameter equal to 9 pixels are 1, and all of those corresponding to the remaining pixels are 0.

More specifically, in the average calculation unit 7, the intensities of the 81 pixels are multiplied by the corresponding coefficients of the coefficient matrix. All the products are summed, and the sum is divided by 20, which is the sum of the coefficients.

When this coefficient matrix is used, the average calculation unit 7 calculates the weighted average over the kernel based on the intensities of the pixels on the circle having a diameter equal to 9 pixels.

As a result, the contaminant-detecting apparatus for calculating the weighted average over the kernel as described above can selectively decrease a false-reject signal due to fluctuations in density in a kernel having a diameter equal to about 9 pixels, and can improve the contaminant detection sensitivity.

In fine, this embodiment is particularly effective for a special application where a contaminant having a size almost equal to the diameter is to be detected.

In this case, in the actual calculation, when the coefficient of the coefficient matrix is 0, no calculation is performed, so that the number of times the sum-of-product operation is performed to calculate the average can be reduced.

More specifically, in this embodiment, about ¾ the coefficients are 0, and about ¼ the elements that remain are 1. Since the number of times of the calculating operation can be reduced to about ¼ that of the seventh embodiment, higher-speed processing can be performed accordingly.

The twelfth embodiment of the present invention will be described.

In the twelfth embodiment, the arrangement of the apparatus is the same as that of the first or second embodiment, and is different from that of the first or second embodiment in the coefficient matrix which is used in an average calculation unit 7 that calculates the weighted average over the kernel.

The average calculation unit 7 calculates the weighted average over the kernel of a 11×11 pixel kernel around the given pixel by using, e.g., a coefficient matrix having coefficients as shown in FIG. 24.

The calculation of the weighted average over the kernel is performed in accordance with the following procedure.

More specifically, the logarithms of the intensities of the respective ones of the 11×11 pixels=121 pixels are multiplied by the corresponding coefficients of the coefficient matrix. All the products are summed, and the sum is divided by 44, which is the sum of the coefficients.

When this coefficient matrix is used, the average calculation unit 7 calculates the weighted average over the kernel by using the intensities of all the pixels around the given pixel in 11×11 pixel kernel.

As a result, the contaminant-detecting apparatus for calculating the weighted average over the kernel as described above can decrease a false-reject signal caused by fluctuations in density in a kernel equal to 11×11 pixels, and effectively detects a specific contaminant which can be mixed in a specific product to be tested, as described earlier with reference to FIG. 15, so that the contaminant detection sensitivity is improved.

The thirteenth embodiment of the present invention will be described.

In the thirteenth embodiment, the arrangement of the apparatus is the same as that of the first or second embodiment, and is different from that of the first or second embodiment in the coefficient matrix which is used in an average calculation unit 7 that calculates the weighted average over the kernel.

As shown in FIG. 25, in the coefficient matrix of the average calculation unit 7 that calculates the weighted average over the kernel used in this embodiment, all of the 11×11=121 elements are 1.

More specifically, in the average calculation unit 7, the intensities of all the 121 pixels are multiplied by the coefficients 1 of the coefficient matrix. All the products are summed, and the sum is divided by 121, which is the sum of the coefficients.

When this coefficient matrix is used, the average calculation unit 7 calculates the weighted average over the kernel by using the intensities of all the pixels around the given pixel in the 11×11 pixel kernel.

As a consequence, the contaminant-detecting apparatus for calculating the weighted average over the kernel as described above can decrease a false-reject signal arising from fluctuations in density of a kernel equal to about 11×11 pixels, and can improve the contaminant detection sensitivity.

The fourteenth embodiment of the present invention will be described.

In the fourteenth embodiment, the arrangement of the apparatus is the same as that of the first or second embodiment, and is different from that of the first or second embodiment in the coefficient matrix which is used in an average calculation unit 7 that calculates the weighted average over the kernel.

As shown in FIG. 26, in the coefficient matrix of the average calculation unit 7 that calculates the weighted average over the kernel used in this embodiment, the 11×11=121 elements of the coefficient matrix form a checker-board pattern in which the elements of each row are alternately 1 and 0 and the elements of each column are alternately 1 and 0.

More specifically, in the average calculation unit 7, the intensities of the 121 pixels are multiplied by the corresponding coefficients of the coefficient matrix. All the products are summed, and the sum is divided by 61, which is the sum of the coefficients.

When this coefficient matrix is used, the average calculation unit 7 calculates the weighted average over the kernel based on the intensities of every other pixels around the given pixel in the 11×11 pixel kernel.

Consequently, the contaminant-detecting apparatus for calculating the weighted average over the kernel as described above can decrease a false-reject signal caused by fluctuations in density of a kernel equal to about 11×11 pixels, and can improve the contaminant detection sensitivity.

In this case, in the actual calculation, when the coefficient of the coefficient matrix is 0, no calculation is performed, so that the number of times the sum-of-product operation is performed to calculate the average can be reduced.

More specifically, in this embodiment, about half the coefficients are 0. Since the number of times of the calculating operation can be reduced to about half that of the twelfth embodiment, higher-speed processing can be performed accordingly.

The fifteenth embodiment of the present invention will be described.

In the fifteenth embodiment, the arrangement of the apparatus is the same as that of the first or second embodiment, and is different from that of the first or second embodiment in the coefficient matrix which is used in an average calculation unit 7 that calculates the weighted average over the kernel.

As shown in FIG. 27, in the coefficient matrix of the average calculation unit 7 that calculates the weighted average over the kernel used in this embodiment, of the 11×11=121 elements of the coefficient matrix, all the elements of the first and last rows are 1, all the elements of the first and last columns are 1, and all the remaining elements are 0.

More specifically, in the average calculation unit 7, the intensities of the 121 pixels are multiplied by the corresponding coefficients of the coefficient matrix. All the products are summed, and the sum is divided by 40, which is the sum of the coefficients.

When this coefficient matrix is used, the average calculation unit 7 calculates the weighted average over the kernel based on the intensities of the pixels on the circumference of the 11×11 pixel kernel.

As a result, the contaminant-detecting apparatus for calculating the weighted average over the kernel as described above can selectively decrease a false-reject signal resulting from fluctuations in density of a kernel, in a product to be tested, with sides each substantially equal to about 11 pixels, and can improve the contaminant detection sensitivity.

In fine, this embodiment is particularly effective for a special application where an almost-square contaminant with sides each having a length equal to about 11 pixels is to be detected.

In this case, in the actual calculation, when the coefficient of the coefficient matrix is 0, no calculation is performed, so that the number of times the sum-of-product operation is performed to calculate the average can be reduced.

More specifically, in this embodiment, about half the coefficients are 0. Since the number of times of the calculating operation can be reduced to about half that of the twelfth embodiment, higher-speed processing can be performed accordingly.

The sixteenth embodiment of the present invention will be described.

In the sixteenth embodiment, the arrangement of the apparatus is the same as that of the first or second embodiment, and is different from that of the first or second embodiment in the coefficient matrix which is used in an average calculation unit 7 that calculates the weighted average over the kernel.

As shown in FIG. 28, in the coefficient matrix of the average calculation unit 7 that calculates the weighted average over the kernel used in this embodiment, of the 11×11=121 elements of the coefficient matrix, those corresponding to the pixels on the circle having a diameter equal to 11 pixels are 1, and all of those corresponding to the remaining pixels are 0.

More specifically, in the average calculation unit 7, the intensities of the 121 pixels are multiplied by the corresponding coefficients of the coefficient matrix. All the products are summed, and the sum is divided by 28, which is the sum of the coefficients.

When this coefficient matrix is used, the average calculation unit 7 calculates the weighted average over the kernel based on the intensities of the pixels on the circle having a diameter equal to 11 pixels.

Therefore, the contaminant-detecting apparatus for calculating the weighted average over the kernel as described above can selectively decrease a false-reject signal caused by fluctuations in density of a kernel, in a product to be tested, with a diameter substantially equal to about 11 pixels, and can improve the contaminant detection sensitivity.

In fine, this embodiment is particularly effective for a special application where a contaminant having a size nearly equal to the diameter is to be detected.

In this case, in the actual calculation, when the coefficient of the coefficient matrix is 0, no calculation is performed, so that the number of times the sum-of-product operation is performed to calculate the average can be reduced.

More specifically, in this embodiment, about ¾ the coefficients are 0, and about ¼ the coefficients that remain are 1. Since the number of times of the calculating operation can be reduced to about ¼ that of the first embodiment, higher-speed processing can be performed accordingly.

Examples of the product to be tested as the target of the present invention include food, food materials, beverages, pharmaceuticals, clothing, textile products (including bedding), paper products, hygienic articles, detergents, cosmetics, chemicals, plastic molded articles, plastic sheets, and rubber molded articles.

These products to be tested may be unpacked, or may be packed in a package made of paper, plastic, an aluminum foil, an aluminum can, or the like.

Examples of contaminants that can be detected by the present invention, among the contaminants that might be mixed in these products to be tested, include metal, stone, glass, hard bone, plastic, and rubber (although the detectable range and size differ depending on the inspection target).

As has been described above in detail, according to the present invention, since the apparatus exploits an image processing algorithm using a kernel equal to or larger than 7×7 pixels, to use of which is not contemplated in the conventional contaminant-detecting apparatus, the false-reject signal can be decreased, and a high-selectivity, high-sensitivity contaminant-detecting apparatus can be provided.

We claim:

1. A high-selectivity, high-sensitivity contaminant-detecting apparatus for effectively suppressing a false-reject signal, comprising conveying means for conveying a product to be tested in a predetermined convey direction, an X-ray source means for radiating X-rays toward the product to be tested which is being conveyed by said conveying means, X-ray detecting means for detecting the X-rays transmitted through the product to be tested, said X-ray detecting means having an X-ray detection unit with a predetermined detection unit width in a direction perpendicularly intersecting the predetermined convey direction, storage means for storing a two-dimensional distribution of an X-ray intensity detected by said X-ray detecting means as a transmission image in units of pixels, average calculating means for performing a sum-of-product operation for a kernel, which is not smaller than 7×7 pixels and not larger than (a pixel count corresponding to ½ the predetermined X-ray detection unit width)×(a pixel count corresponding to ½ the predetermined X-ray detection unit width), the kernel including a target pixel, in units of pixels of the transmission image stored in said storage means by using a predetermined coefficient matrix, thereby calculating a weighted average over the kernel, difference calculating means for calculating a difference between the X-ray intensity of the target pixel of the transmission image stored in said storage means and the weighted average over the kernel of the target pixel which is calculated by said average calculating means, and determining means for comparing the difference calculated by said difference calculating means with predetermined criteria, thereby determining presence/absence of a contaminant in the product to be tested.

2. A high-selectivity, high-sensitivity contaminant-detecting apparatus for effectively suppressing a false-reject signal, comprising conveying means for conveying a product to be tested in a predetermined convey direction, an X-ray source means for radiating X-rays toward the product to be tested which is being conveyed by said conveying means, X-ray detecting means for detecting the X-rays transmitted through the product to be tested, said X-ray detecting means having an X-ray detection unit with a predetermined detection unit width in a direction perpendicularly intersecting the predetermined convey direction, storage means for storing a two-dimensional distribution of an X-ray intensity detected by said X-ray detecting means as a transmission image in units of pixels, average calculating means for performing a sum-of-product operation for a kernel, which is not smaller than 9×9 pixels and not larger than (a pixel count corresponding to ½ the predetermined X-ray detection unit width)×(a pixel count corresponding to ½ the predetermined X-ray detection unit width), the kernel including a target pixel, in units of pixels of said transmission image stored in said storage means by using a predetermined coefficient matrix, thereby calculating a weighted average over the kernel, difference calculating means for calculating a difference between the X-ray intensity of the target pixel of the transmission image stored in said storage means and the weighted average over the kernel of the target pixel which is calculated by said average calculating means, and determining means for comparing the difference calculated by said difference calculating means with predetermined criteria, thereby determining presence/absence of a contaminant in the product to be tested.

3. A high-selectivity, high-sensitivity contaminant-detecting apparatus for effectively suppressing a false-reject signal, comprising conveying means for conveying a product to be tested in a predetermined convey direction, an X-ray source means for radiating X-rays toward the product to be tested which is being conveyed by said conveying means, X-ray detecting means for detecting the X-rays transmitted through the product to be tested, said X-ray detecting means having an X-ray detection unit with a predetermined detection unit width in a direction perpendicularly intersecting the predetermined convey direction, storage means for storing a two-dimensional distribution of an X-ray intensity detected by said X-ray detecting means as a transmission image in units of pixels, average calculating means for performing a sum-of-product operation for a kernel, which is not smaller than 11×11 pixels and not larger than (a pixel count corresponding to ½ the predetermined X-ray detection unit width)×(a pixel count corresponding to ½ the predetermined X-ray detection unit width), the kernel including a target pixel, in units of pixels of the transmission image stored in said storage means by using a predetermined coefficient matrix, thereby calculating a weighted average over the kernel, difference calculating means for calculating a difference between the X-ray intensity of the target pixel of the transmission image stored in said storage means and the weighted average over the kernel of the target pixel which is calculated by said average calculating means, and determining means for comparing the difference calculated by said difference calculating means with predetermined criteria, thereby determining presence/absence of a contaminant in the product to be tested.

4. A contaminant-detecting apparatus according to claim 1, characterized in that said average calculating means has logarithm converting means for converting the X-ray intensity of each of the pixels of the transmission image into a logarithm and calculates the weighted average over the kernel based on the logarithm of the kernel by using the logarithm of the X-ray intensity of each pixel of the transmission image obtained by conversion with said logarithm converting means, and said difference calculating means calculates a difference between the logarithm of the X-ray intensity of the target pixel with the weighted average over the kernel in logarithm of the target pixel.

5. A contaminant-detecting apparatus according to claim 2, characterized in that said average calculating means has logarithm converting means for converting the X-ray intensity of each of the pixels of the transmission image into a logarithm and calculates the weighted average over the kernel based on the logarithm of the kernel by using the logarithm of the X-ray intensity of each pixel of the transmission image obtained by conversion with said logarithm converting means, and said difference calculating means calculates a difference between the logarithm of the X-ray intensity of the target pixel with the weighted average over the kernel in logarithm of the target pixel.

6. A contaminant-detecting apparatus according to claim 3, characterized in that said average calculating means has logarithm converting means for converting the X-ray intensity of each of the pixels of the transmission image into a logarithm and calculates the weighted average over the kernel based on the logarithm of the kernel by using the logarithm of the X-ray intensity of each pixel of the transmission image obtained by conversion with said logarithm converting means, and said difference calculating means calculates a difference between the logarithm of the X-ray intensity of the target pixel with the weighted average over the kernel in logarithm of the target pixel.

7. A contaminant-detecting apparatus according to any one of claims 1 to 6, characterized in that all elements of the coefficient matrix are 1.

8. A contaminant-detecting apparatus according to any one of claims 1 to 6, characterized in that elements of each row of the coefficient matrix are alternately 1 and 0 and elements of each column thereof are alternately 1 and 0, thus forming a checker-board pattern.

9. A contaminant-detecting apparatus according to any one of claims 1 to 6, characterized in that all elements of first and last rows of the coefficient matrix are 1, all elements of first and last columns thereof are 1, and all remaining elements are 0.

10. A contaminant-detecting apparatus according to any one of claims 1 to 6, characterized in that of elements of the coefficient matrix, all of elements corresponding to a circular circumference, among circles in the kernel that have the target pixel as a center, having a maximum diameter are 1, and all of remaining elements are 0.

11. A contaminant-detecting apparatus according to any one of claims 1 to 6, characterized in that the product to be tested contains at least one element selected from food, a food material, a beverage, a pharmaceutical, clothing, a textile product (including bedding), a hygienic article, a paper product, a detergent, a cosmetic, a chemical, a plastic molded article, a plastic sheet, and a rubber molded article.

* * * * *